(12) United States Patent
Desmaris et al.

(10) Patent No.: US 7,090,836 B2
(45) Date of Patent: Aug. 15, 2006

(54) VECTOR FOR EXPRESSING α-L-IDURONIDASE AND METHOD OF TREATING MPS I BY STEREOTACTIC INJECTION INTO THE BRAIN OF A MAMMAL

(75) Inventors: Nathalie Desmaris, Roissey en Brie (FR); Jean Michel Heard, Paris (FR)

(73) Assignee: Institut Pasteur, Paris (FR)

( * ) Notice: Subject to any disclaimer, the term of this patent is extended or adjusted under 35 U.S.C. 154(b) by 127 days.

(21) Appl. No.: 10/176,066

(22) Filed: Jun. 21, 2002

(65) Prior Publication Data

US 2004/0023218 A1 Feb. 5, 2004

(51) Int. Cl.
*A01N 63/00* (2006.01)
*A01N 65/00* (2006.01)
*A01N 43/04* (2006.01)
*A01N 31/70* (2006.01)
*A61K 31/70* (2006.01)

(52) U.S. Cl. ............... 424/93.1; 514/44; 435/320.1; 536/23.1; 536/23.5

(58) Field of Classification Search ......... 514/44; 424/93.2, 93.21, 93.1; 435/320.1, 325; 536/23.1, 536/23.5, 23.4
See application file for complete search history.

(56) References Cited

U.S. PATENT DOCUMENTS

| | | | |
|---|---|---|---|
| 5,753,500 A * | 5/1998 | Shenk et al. | 435/320.1 |
| 5,843,742 A | 12/1998 | Natsoulis et al. | 435/172.3 |
| 5,872,005 A * | 2/1999 | Wang et al. | 435/320.1 |
| 6,066,626 A * | 5/2000 | Yew et al. | 514/44 |
| 6,136,597 A | 10/2000 | Hope et al. | 435/325 |
| 6,328,958 B1 * | 12/2001 | Amalfitano et al. | 424/93.2 |
| 6,582,692 B1 * | 6/2003 | Podsakoff et al. | 424/93.2 |

FOREIGN PATENT DOCUMENTS

| | | |
|---|---|---|
| WO | WO 96 18727 | 6/1996 |
| WO | WO 99 14310 | 3/1999 |
| WO | WO 99 61066 | 12/1999 |

OTHER PUBLICATIONS

Eck, et al. (1996) The Pharmacological Basis of Therapeutics, Ninth Ed., pp. 77-101, McGraw-Hill, N.Y.*
Kaye, et al. (Aug. 2002) Neurol. Clin. 20(3): 897-901.*
Bosch, et al. (2000) Molecular Therapy, 1(1): 63-70.*
Consiglio, et al. (2001) Nature Medicine, 7(3): 310-16.*
Frisella, et al. (2001) Mol. Ther. 3(3): 351-58.*
Weber, et al (2001) Prot. Exp. Purif., 21: 251-59.*
Naldini, et al (1996) Proc. Natl. Acad. Sci., USA., 93: 11382-88.*
Scott, et al. (1991) Proc. Natl. Acad. Sci., USA., 88: 9695-99.*
Zhao, et al. (1996) Proc. Natl. Acad. Sci., USA, 93: 6101-05*
Adra, et al. (1987) Gene, 60: 65-74.*
Kordower, J. H., Emborg, M. E., Bloch, J., Ma, S. Y., Chu, Y., Leventhal, L., McBride, J., Chen, E. Y., Palfi, S., Roitberg, B. Z., et al. (2000). Neurodegeneration prevented by lentiviral vector delivery of GDNF in primate models of Parkinson's disease. Science 290, 767-773.
Daly, T.M., Vogler, C., Levy, B., Haskins, M. E., and Sands, M. S. (1999). Neonatal gene transfer leads to widespread correction of pathology in a murine model of lysosomal storage disease. Proc. Natl. Acad. Sci. USA 96, 2296-2300.

\* cited by examiner

*Primary Examiner*—Joseph Woitach
*Assistant Examiner*—Robert M. Kelly
(74) *Attorney, Agent, or Firm*—Finnegan, Henderson, Farabow, Garrett & Dunner, LLP

(57) ABSTRACT

A purified nucleic acid molecule capable of expressing a lysosomal enzyme, e.g., iduronidase or arylsulphatase, is provided. The molecule includes a promoter of the phosphoglycerate kinase gene to facilitate expression of the lysosomal enzyme in the brain. Expressing the lysosomal enzyme in the brain of patients with lysosomal storage diseases, such as mucopolysaccharidosis, provides treatment for the neurological aspects of these diseases. The invention also provides a method of gene therapy for lysosomal storage diseases by administering the nucleic acid molecule in the form of a vector.

6 Claims, 4 Drawing Sheets

VECTOR FOR EXPRESSING α-L-IDURONIDASE AND METHOD OF TREATING MPS I BY STEREOTACTIC INJECTION INTO THE BRAIN OF A MAMMAL

BACKGROUND OF THE INVENTION

This invention relates to a purified nucleic acid molecule, which is capable of expressing a lysosomal enzyme, wherein the nucleic acid molecule comprises at least a sequence coding for the lysosomal enzyme and a promoter highly active in the brain inserted upstream from the sequence.

Lysosomal storage diseases form a group of more than 30 metabolic disorders in which the function of one or several lysosomal hydrolases is deficient. Although the prevalence of each disease is low, prevalence of lysosomal storage diseases as a whole may be equivalent to that of cystic fibrosis in the general population (1:2500). In France, the most frequent lysosomal storage diseases are Gaucher type I disease, Hurler disease (MPS I), Hunter disease (MPS II), Sanfilippo disease (MPS III) and metachromatic leucodystrophy (MLD). They represent 10 to 50 births every year. With the exception of Gaucher type I disease, Pompe disease, Fabry disease and mild forms of MPS I, there is no etiological treatment available for lysosomal storage diseases so far. Bone marrow transplantation (BMT), which may be an option in some MPS I patients, is not effective in MPS III and MLD.

Lysosomal enzyme deficiencies induce the accumulation of intermediate catabolites in lysosomes, which progressively alters cell function and survival. Although deficiencies affect every tissue, clinical expression varies depending on the missing enzyme. Neurological symptoms are often predominant. They include severe motor impairments and mental retardation. Histopathology reveals characteristic vacuolizations in both neurons, glia and perivascular cells, without known predominance in specific locations. Other frequent symptoms include hepatomegaly, skeletal abnormalities, corneal clouding and respiratory, cardiac or renal dysfunctions leading to premature death. There is a need in the art for a treatment of the central nervous system pathology in lysosomal storage diseases in which neurological symptoms are either predominant, as in MPS III and MLD, or highly determinant for the clinical prognosis, as in MPS I. MPS I and MPS IIIb are autosomal recessive lysosomal storage diseases classified among mucopolysaccharidosis. These diseases are caused by a defect in the degradation pathway of glycosaminoglycans (GAGs). In MPS I and MPS IIIb, the degradation of heparan sulfates is interrupted by the deficiency of α-L-iduronidase (IDUA) and α-N-acetyl-glucosaminidase (NaGlu), respectively. Complete IDUA deficiency is associated with mutations W402X, Q70X and is responsible for severe forms of MPS I, in which skeletal abnormalities can be recognized at birth and neurological symptoms may occur before the age of 2–3 years. Milder forms exist in which the neurological disease is delayed and less severe (mild forms of MPS I or Hurler-Scheie disease) or even absent (Scheie disease). Except a frequent hepatomegaly, peripheral abnormalities are absent in MPS IIIb. Symptomatology appears in children between the age 2 and 6 as behavioral troubles, which progressively lead to a severe mental and motor degradation.

MLD is an autosomal recessive lysosomal storage disorder classified among the lipidoses. It is caused by a deficiency of arylsulphatase A (ASA) that leads to demyelination in the central and peripheral nervous system. Deficiency of ASA causes intralysosomal storage of the sphingolipid cerebroside sulphate. This lipid is abundant in myelin and its accumulation leads to the death of oligodendrocytes. ASA catalyses the first step in the degradation of the sphingolipid cerebrosisde 3-sulphate by removing the sulphate from the polar head of this lipid, which is a galactose 3-sulphate moiety. If this step does not occur, owing to a deficiency of ASA, this lipid cannot be degraded and accumulates into lysosomes. MLD may appear at any age. The three main clinical forms that correlate with the genotype can be distinguished: infantile, juvenile and adult forms. Allogenic BMT has no effect in the most frequent infantile form of MLD (>60% of the MLD cases) and limited effect in juvenile MLD.

SUMMARY OF THE INVENTION

This invention provides a purified nucleic acid molecule, which is capable of expressing a lysosomal enzyme, wherein the nucleic acid molecule comprises at least a sequence coding for the lysosomal enzyme and a promoter highly active in the brain inserted upstream from the sequence. The nucleic acid molecule can further comprise a posttranscriptional regulatory element inserted downstream from the sequence. In one embodiment, the promoter highly active in the brain is the promoter of the phosphoglycerate kinase gene. In another embodiment, the posttranscriptional regulatory element is a hepatitis virus posttranscriptional regulatory element. The sequence can code, for example, for an iduronidase (IDUA) or an arylsulphatase (ASA).

In a further embodiment of the invention, the nucleic acid molecule further comprises at least one repeated adeno-associated virus (AAV) sequence involved in packaging and genome replication placed upstream from the promoter and/or downstream from the sequence coding for the lysosomal enzyme.

In another embodiment, the nucleic acid molecule further comprises at least one repeated AAV sequence involved in packaging and genome replication placed upstream from the promoter and/or downstream from the sequence coding for the posttranscriptional regulatory element.

This invention also provides one or more recombinant *E coli* bacteria comprising a nucleic acid sequence encoding a lysosomal enzyme and a promoter active in the brain, inserted upstream from said sequence, wherein the recombinant bacteria have been deposited with the Collection Nationale de Cultures de Microorganismes (C.N.C.M.), 28, rue du Docteur Roux 75724 Paris Cédex 15, France on Jun. 20, 2002 under the reference I-2891.

This invention also provides one or more recombinant *E. coli* bacteria comprising a nucleic acid sequence encoding a lysosomal enzyme and a promoter active in the brain, inserted upstream from said sequence, wherein the recombinant bacteria have been deposited with the Collection Nationale De Cultures de Microorganismes (C.N.C.M.) 28, rue du Docteur Roux, 75724 Paris Cédex 15, France on Jun. 20, 2002 under the reference I-2892.

In addition, this invention provides a vector for the expression of a lysosomal enzyme, wherein the vector comprises the nucleic acid molecule of the invention.

The vector is, for example, an adenovirus vector (AAV), or a lentivirus vector.

Still further, this invention provides a cell transformed with the nucleic acid molecule of the invention. The cell can be a mammalian cell, and the cell can be transformed ex vivo.

This invention provides a method for preventing or treating a lysosomal storage disease in a mammal, wherein the method comprises administering the nucleic acid molecule of the invention to a mammalian host. In one embodiment, the mammal is a human. The disease can be, for example, MPS I or MPS IIIb.

This invention also provides a method for preventing or treating a lysosomal storage disease in a mammal, wherein the method comprises administering a vector of the invention to a mammalian host. The vector can be administered by stereotactic method.

This invention also provides a method for preventing or treating a lysosomal storage disease in a mammal, wherein the method comprises the transfer of a cell of the invention into said mammalian host.

BRIEF DESCRIPTION OF THE DRAWINGS

This invention will be described with reference to the drawings in which.

The structures of the AV-PGK-IDUA and the AAV-PGK-NaGLU vectors are as follows. Present at both extremities are repeated AAV sequences which are utilized in packaging and genome replication (ITR). In the AAV-PGK-IDUA and the AAV-PGK-NaGLU vectors, these ITR sequences consist of 181 bp from plasmid pSUB 201 isolated by Dr. R. Samulski (Samulski et al., 1987).

The promoter of the mouse phosphoglycerate kinase gene (Adra et al., 1987) was inserted downstream of the 5' ITR. This promoter (mPGK) comprises a 500 bp XbaI/MluI fragment from plasmid M48 (Salvetti et al., 1995) and is highly active in brain cells (Kordower et al., 2000).

A human cDNA encoding a lysosomal enzyme was inserted downstream of the mouse PGK promoter. In the AAV-PGK-IDUA vector, this cDNA encodes human IDUA, and was inserted as a 2165 bp MluI/NheI fragment of plasmid M48. This cDNA was isolated by the inventors, using the published sequence (Scott et al., 1991). In the AAV-PGK-NaGLU vector, this cDNA encodes human NaGlu, which was isolated by Professor E. Neufeld (UCLA) as described (Zhao et al., 1996).

A woodchuck enhancer (WPRE) sequence was inserted downstream of the human cDNA (Zufferey et al., 1999). This 639 bp sequence, originally described in the laboratory of Dr. D. Trono (CMU Genève), was isolated from a plasmid provided to the inventors by Dr. Naldini (Università di Torino). A polyadenylation site from the bovine growth hormone gene was inserted downstream of WPRE. This site is a 382 bp sequence originally described by Goodwin and Rottman (1992).

Treated mice were sacrificed 2, 6, 16, 20, or 26 weeks after vector injection. Coronal 100 µm or 1 mm brain sections were prepared and IDUA activity was measured in tissue extract from these sections. Data are shown as a schematic representation of the brain and of the analyzed sections. Activity levels are shown according to the indicated color code. The vector injection site is indicated as a black dot in the right hemisphere. Results demonstrate IDUA spreading in brain tissues from the injection site to the ipsi and contralateral hemispheres.

Figure 3:
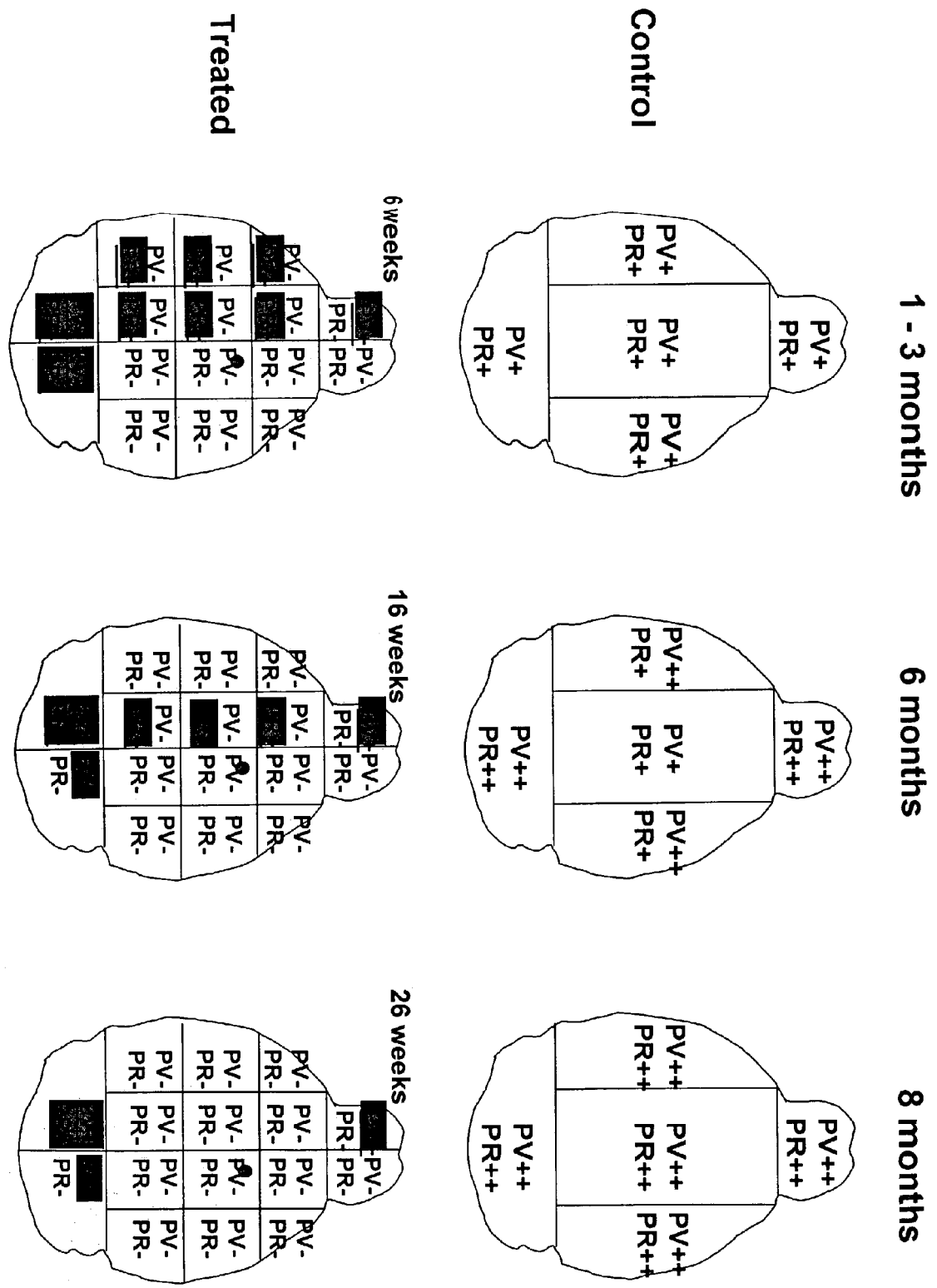

FIG. 3. Disease correction in treated MPS I mouse brain.

Samples were taken from mouse brain section, fixed with glutaradehyde and embedded in Epoxy. Semi-thin sections (1 µm) were prepared and stained with toluidine blue. The intensity of lysosomal storage lesions in the various analyzed part of the brains is indicated as: −, lesions were not observed; +, moderate lesions; or ++, severe lesions. PV: perivascular area, PR: parenchymal area. Controls are untreated MPS I mice. Lesions were detected in these animals as early as one month of age and progressively aggravated with time. Treated animals analyzed after 6 weeks were 3 month old, after 16 weeks, 6 month old and after 26 weeks, 8 month old. Data show a progressive regression of the lesions with time in treated mice.

Figure 4:
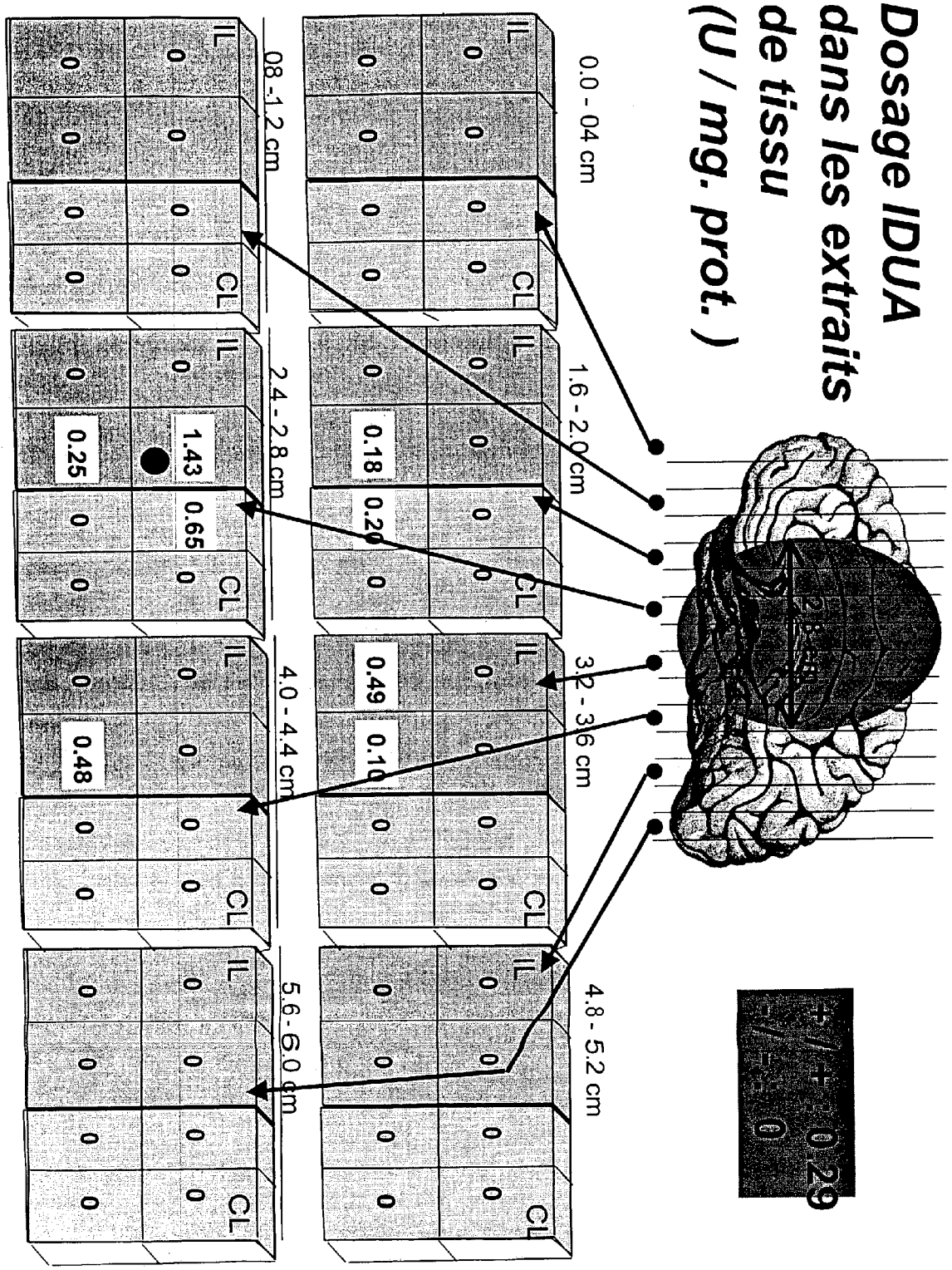

FIG. 4. Enzyme spreading in MPS I dog brain.

Brain was cut into 16 slices. Every second slice was used for IDUA detection. The alternate slice was used for histology. Each slice was divided into four samples for each hemisphere, from which tissue extracts were prepared for IDUA assay. A total of 64 samples were measured. The site of vector injection is indicated by a black dot. Data are enzyme activity levels for the injected (IL) and contralateral (CL) hemispheres.

DETAILED DESCRIPTION OF PREFERRED EMBODIMENTS

Lysosomal disorders in general, and MPS I in particular have long been considered amenable to treatment by exogenous enzyme that would enter the deficient cells by endocytosis (Fratantoni et al., 1968; Kaplan et al., 1977; Sando and Neufeld, 1977). Exogenous enzyme eliminates the abnormal accumulation of GAGs in cultures MPS I fibroblasts. High efficient enzyme uptake relies on the presence of specific sugars, which are recognized by their cognate receptor. These include the mannose-6-phosphate receptor (M6PR) which is ubiquitously expressed, the galactose receptor of hepatocytes and the mannose receptor of macrophages. The latter is used with success for treating Gaucher type I patients with a modified glucocerebrosidase enzyme preparation targeting the macrophages (Barton et al., 1991; Grabowski et al., 1998). Trials have recently been performed with enzyme targeting the M6PR in patients with diseases that do not affect the brain, as Fabry disease (Eng et al., 2000; Schiffmann et al., 2000), Pompe disease (van der Hout et al., 2000) and mild forms of MPS I (Scheie disease).

As the infused enzyme does not cross the blood brain barrier, no benefit can be expected on brain damages. Thus, etiological treatment is currently proposed only for patients in whom a neurological disease is not anticipated. In the most frequent situation of a disease known to affect the brain, no treatment can be proposed at the present time. Gene therapy appears as the only option that could lead to a therapeutic strategy targeted to the brain.

Various approaches have been considered with the aim to obtain in situ enzyme delivery in the brain parenchyme. Cells genetically-modified ex vivo in order to over-express and secrete the missing lysosomal enzyme were implanted in the brain. Direct intracranial injections of gene transfer vectors by stereotactic methods were performed with the aim to inducing enzyme over-expression and secretion from resident neurons and glial cells.

These experiments were performed in a mouse model of lysosomal storage diseases. The β-glucuronidase deficient mouse (MPS VII) resumes the clinical features of human mucopolysaccharidosis, including abnormal skeletal development, corneal clouding and deafness (Birkenmeier et al., 1989). Considerable lysosomal storage occurs in every tissue, and especially in the brain. Animals die around 6 months of age, apparently from both progressive neurological degradation and locomotor disability. Animals were either engrafted with cell genetically-modified to over-express β-glucuronidase, or received a functional β-glucuronidase cDNA by the mean of a gene transfer vector which could be adenovirus vectors, AAV vectors or lentivirus vectors. Consistent results provided evidence that enzyme expression was not restricted to the area where the cells or the vector had been injected (Ghodsi et al., 1998; Snyder et al., 1995; Taylor and Wolfe, 1997). Activity could be demonstrated in far remote locations, including in the contralateral hemisphere when injection was unilateral. These data indicated that brain cells were able to take up enzyme from the extracellular environment and more importantly, suggest that β-glucuronidase could be transported over long distances in the brain by retrograde axonal transport. These studies also demonstrated that gene therapy could prevent the development of lesions and reverse pre-existing damages.

The feasibility of preventing the development lesions was demonstrated in newborn MPS VII mice. This was shown either in animals engrafted in situ with immortalized enzyme-secreting cells (Snyder et al., 1995); or injected intravenously at birth with purified enzyme (Sands et al., 1994; Sands et al., 1997; Vogler et al., 1993; Vogler et al., 1996) or with a recombinant adeno-associated vector encoding β-glucuronidase (Daly et al., 1999a; Daly et al., 1999b).

The reversion of pre-existing lesions in adult animals has also been demonstrated. Transient correction was reported after the engraftment of enzyme-secreting primary cells (Taylor and Wolfe, 1997) or the in situ injection of an adenovirus vector (Ghodsi et al., 1998; Stein et al., 1999). Others and ourselves have shown a sustained correction after the in situ injection of an adeno-associated virus (AAV) vector (Bosch et al., 2000a; Skorupa et al., 1999). Using lentivirus-based vector we have documented enzyme delivery and reversal of pathology in the entire brain of MPS VII mice (Bosch et al., 2000b).

The efficacy of direct gene transfer into the brain has recently been documented another mouse model of lysosomal storage disease. The MLD mouse has been created by the selective destruction of the ASA gene. Mice develop a mild pathology reminiscent of that associated with human MLD after 8 to 10 months, with typical storage lesions in the white matter (Hess et al., 1996). This pathology can locally be prevented and reversed by the delivery of lentivirus-derived gene transfer vector encoding ASA in the fimbria (Consiglio et al., 2001). A controversy remains about whether this treatment actually improves mouse behavior and with regards to the relevance of correcting fimbria neurons in a disease that is mostly a demyelinating process.

Achievements in the brain of MPS VII mice stereotactically injected with AAV or lentivirus vector reached the requisites for an effective treatment. The current issue consists in passing through the various stages from mouse experimentation to clinical application. As gene therapy targeted to the brain is very innovative, these stages must be cautiously designed.

As MPS I affects both the central nervous system and the peripheral organs, gene therapy trial targeted to the brain in this disease will have to be combined with enzyme replacement therapy in the periphery. The choice of MPS IIIb and MLD as diseases in which a clinical trial will be considered first, is based on the predominance of neurological symptoms, the relative high frequency of the disorders among lysosomal storage diseases and the absence of efficacy of bone marrow transplantation.

On the other hand, it is important to consider that whereas excellent mouse and dog, models are available for MPS I and MPS IIIb, there is no convenient animal model for MLD. Indeed, the MLD mouse develops late and mild pathology, which delays and hampers accurate assessment of disease correction. Our strategy therefore is to perform most of the preclinical investigations proposed in this program in the available MPS I and MPS IIIb animal models. It is well documented in the literature that MPS I and MPS III share common pathophysiology with MLD. Thus feasibility studies performed in the MPS I and MPS IIIb models will provide relevant information for application in MLD patients.

The final objective of the pre-clinical studies is the design of a phase I/II protocols for the assessment of tolerance and therapeutic potential of intracranial injections of gene transfer vectors in children with MPS I and MPS IIIb. Pre-clinical studies in animal models are mandatory to designing a clinical trial protocol.

Material and Methods

Gene Transfer Vectors

Investigations in MPS I and MPS IIIb mice were performed with the AAV-PGK-IDUA and the AAV-PGK-NaGLU vectors, respectively. These vectors were derived from AAV serotype 2 (AAV-2). Their genomes are similarly organized; the difference between them resides in the expressed cDNA sequence.

A polyadenylation site from the bovine growth hormone gene is inserted downstream of WPRE. This is a 382 bp sequence originally described by Goodwin et al. (Goodwin and Rottman, 1992).

Vector Preparation

Vector stocks were prepared in the Laboratoire de Thépie Génique, CHU Hôtel-Dieu, Nantes, by triple transfection into 293-T cells, as described in Salvetti et al. (Salvetti et al., 1998).

Vector Administration

Vectors were administrated by stereotactic injection in the brain tissue. In the mouse, a single injection of 5 μL containing $2 \times 10^9$ physical particles of AAV vector was performed in the putamen. Animals were treated at 6–8 weeks of age. In dogs, a single intrastriatal 40 μL injection was performed.

Investigations in MPS Mouse Models

MPS I and MPS IIIb mice have been obtained by a selective disruption of the genes coding for α-L-iduronidase (IDUA)(Clarke et al., 1997) and α-N-acetyl-galactosaminidase (NaGlu)(Li et al., 1999), respectively. We obtained these animals from Pr. E. Neufeld (UCLA). Homozygous mutants exhibit a total absence of catalytic activity of the targeted enzymes. They develop typical lysosomal storage pathology over the first 6 months of life, including lysosomal storage lesions in brain cells.

Investigations in MPS I Dogs

A colony of dogs deficient for IDUA has been raised and maintained at the University of Tennessee (Shull et al., 1982; Spellacy et al., 1983). We obtained 10 breeders from Dr. E. Kakis (UCLA). Dogs have been installed in France with the support of the AFM. These animals have a point mutation in the first exon/intron border of the IDUA gene (Menon et al., 1992). Dogs homozygous for the mutation exhibit a total enzyme deficiency. They develop a characteristic Hurler/Scheie disease during the course of their first year of life, associating severe abnormalities of the skeleton and intense lysosomal storage lesions in various tissues, including in the brain (Constantopoulos et al., 1985; Walkley et al., 1988).

MPS I dogs have been extensively studied in the past. Clinical benefit has been demonstrated after allogeneic bone marrow transplantation (Shull et al., 1987). Enzyme infusion in the periphery improves lysosomal storage significantly (Shull et al., 1994). However, all animals develop an immune response against the infused human enzyme (Kakkis et al., 1996; Lutzko et al., 1999). In the absence of any detectable IDUA activity in these animals, it is expected that immunization will occur with the canine enzyme as well. To our knowledge, no attempt has been made so far with the aim to treat the brain pathology in these dogs.

MPS I dogs are genotyped and homozygous animals are transferred to the Centre de Boisbonne of the Ecole Nationale Vétérinaire de Nantes at weaning. Surgery is performed at the Centre de Boisbonne.

Enzyme Activity, Diffusion and Correction of Storage Lesions in MPS I Mouse Brains.

Forty young adult IDUA-deficient MPS I mice received a single intrastriatal injection of the AAV-PGK-IDUA vector. Animals were sacrificed 2, 6, 16, 20 or 26 weeks after injection.

In a first group of treated mice, we measured enzyme activity in tissue extracts from the injected hemisphere, the contralateral hemisphere and the caudal part of the encephalon including the cerebellum and the brain stem. Results are shown in Table 1.

TABLE 1

IDUA activity in brain extracts of normal mice (+/+), heterozygote mice (+/−) and untreated (−/−) or treated IDUA-deficient mutant MPS I mice. Treated mice were sacrificed at 2, 6–16, 20 or 26 weeks after a single vector injection in the striatum.

| | IDUA | |
|---|---|---|
| | BRAIN | CR + BRAINSTEM |
| +/+ | 2.38 ± 0.12 (n = 6) | 2.33 ± 0,47 (n = 3) |
| +/− | 1.23 ± 0.22 (n = 24) | 1.16 ± 0,27 (n = 13) |
| −/− | 0 (n = 14) | 0 (n = 7) |

| | IL | CL |
|---|---|---|
| 2 WKS | | |
| 2-1 | 6 | ND | ND |
| 2-2 | 7.97 | ND | ND |
| 2-3 | 7.93 | 0.38 | 0.55 |
| 2-4 | 8.22 | 0.55 | 0.20 |
| 2-5 | 9.07 | 1.11 | 0.19 |
| 2-6 | 7.8 | 0.1 | 0 |
| 2-7 | 8.9 | 0.4 | 0.8 |
| 6 WKS | | |
| 6-1 | 10 | 0.40 | 0.10 |
| 6-2 | 8.6 | 0.90 | 0.30 |
| 6-3 | 9.41 | 0.44 | 0.44 |
| 6-4 | 9.78 | 0.44 | 0.15 |
| 6-5 | 9.93 | 1.56 | 0.44 |
| 6-6 | 0.85 | 0 | 0 |
| 6-7 | 0.7 | 0.01 | 0 |
| 6-8 | 3.34 | 0 | 0.6 |
| 6-9 | 6.68 | 0.2 | 0 |
| 16 WKS | | |
| 16-1 | 10.5 | 1.5 | 0.30 |
| 16-2 | 2.9 | 0.41 | 0.34 |
| 16-3 | 6.3 | ND | ND |
| 16-4 | 21.7 | 0.53 | 0.35 |
| 16-5 | 9 | 9.7* | 0.18 |
| 16-6 | 0.6 | 0 | 0 |
| 16-7 | 3.59 | 1.18 | 0.12 |
| 16-8 | 6.46 | 0.38 | ND |
| 16-9 | 11.94 | 4.96 | 1.8 |
| 16-10 | 8.55 | 1.36 | 12.15 |
| 16-11 | 0.01 | 0 | 0 |
| 20 WKS | | |
| 20-1 | 1.21 | 0 | 0 |
| 20-2 | 1.74 | 0 | 0 |
| 20-3 | 1.73 | 0.18 | 0 |
| 20-4 | 0 | 0 | 0 |
| 26-5 | 0.53 | 0 | 0 |
| 26 WKS | | |
| 26-1 | 23.6 | 0.20 | 0.53 |
| 26-2 | 3.5 | 0.35 | ND |

TABLE 1-continued

IDUA activity in brain extracts of normal mice (+/+), heterozygote mice (+/−) and untreated (−/−) or treated IDUA-deficient mutant MPS I mice. Treated mice were sacrificed at 2, 6–16, 20 or 26 weeks after a single vector injection in the striatum.

| 26-3 | 17.5 | 0.6 | 0 |
|---|---|---|---|
| 26-4 | 0.42 | 0 | 0 |
| 26-5 | 0.6 | 0 | 0 |
| 26-6 | 5,7 | 0.82 | 0 |
| 26-7 | 0 | 0 | 0 |
| 26-8 | 0.46 | 0 | 0 |
| 26-9 | 2.73 | 0 | 0 |

Figure 1:
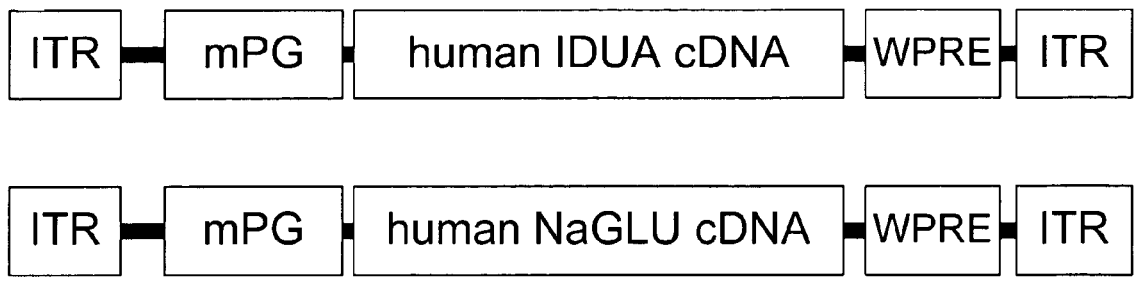
FIG. 1. Structure of the AAV-PGK-IDUA and the AAV-PGK-NaGLU vectors.
Figure 2:
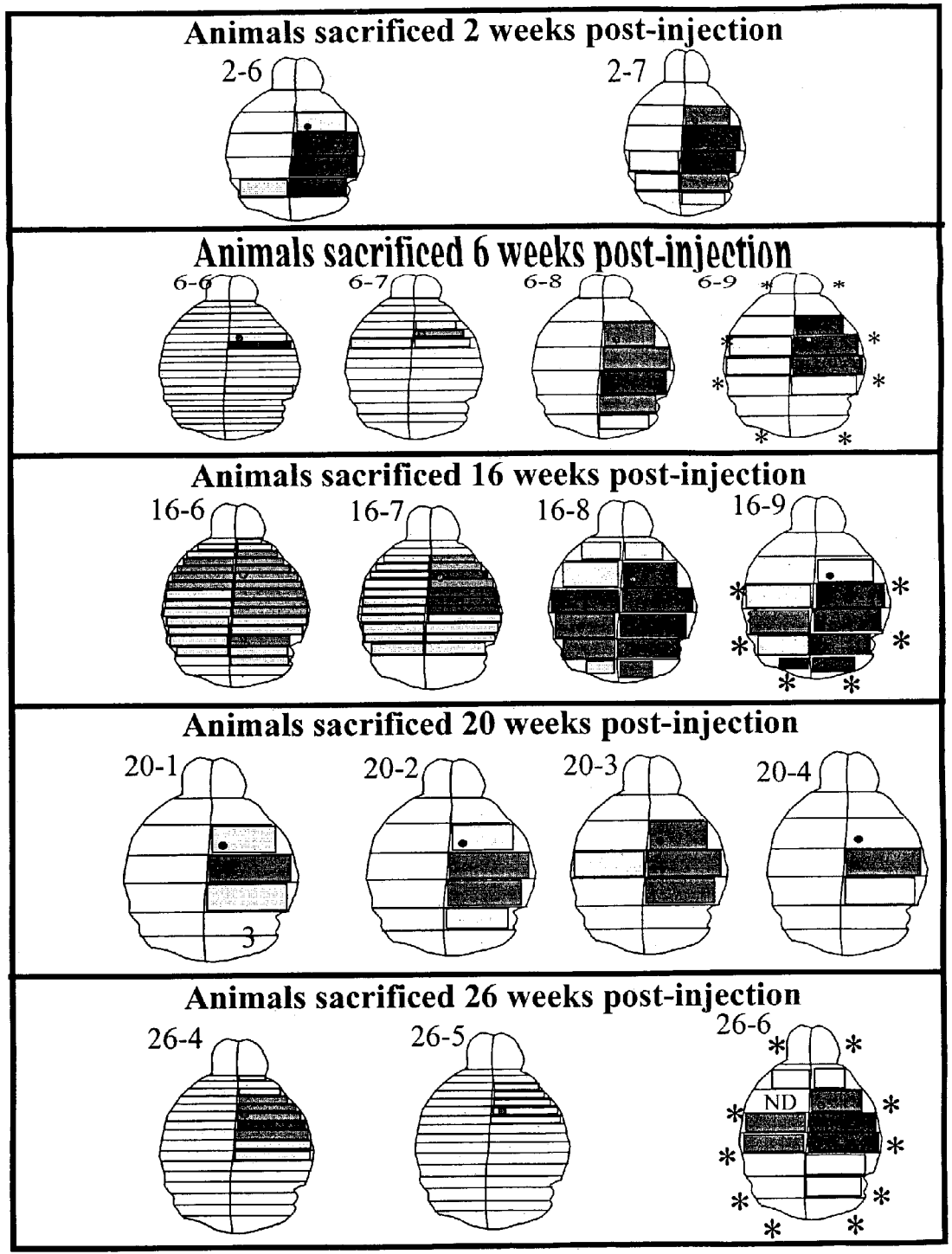
FIG. 2. IDUA spreading in the brain of treated MPS I mice.

These experiments revealed high enzyme activity in the injected hemisphere (3 to 4 folds more than in normal mice), and significant levels in more remote locations (10 to 30% of normal mouse levels). Activities were stable over the 7-month follow up. In a second series of mice, serial coronal brain sections (100 μm or 1 mm) were performed and activity was measured in extracts. This experiment allowed drawing of a precise map of the location of enzyme activity throughout the brain over time. It showed that enzyme progressively spreads, from week 2 to 16, from the injection site to remote locations (FIG. 2). At 16 weeks after injection, in most mice, enzyme activity could be detected all over brain, except in the most rostral and caudal regions of the contralateral hemisphere. A third series of mice was used to examine enzyme activity and disease correction in adjacent coronal sections. It revealed a complete correction of storage lesions in areas where enzyme was detectable, but also in region where the enzyme assay was negative. Corrected areas progressively increased in size with time (FIG. 3). At 26 weeks, only very limited areas of the contralateral olfactive bulb and the cerebellum still showed minimal storage lesions. These results clearly demonstrate that IDUA is produced from cells genetically modified with the AAV-IDUA vector and delivered to far distant locations from the vector injection site. Spreading over the brain increases with time. Enzyme delivery allows a correction the histological lesions associated with the disease. Such an efficient delivery of a lysosomal enzyme in the brain parenchyme has not been reported previously.

Enzyme Activity and Diffusion in the Brain of a MPS I Dog.

A 40 μL injection of the AAV-PGK-IDUA vector was performed in the striatum of one MPS I dog. The animal received cyclosporine for 3 days before treatment and until sacrifice 12 weeks after the injection. For analysis of enzyme spreading in the brain, the entire encephalon was cut in 16 slices and each slice separated in four sections. Tissue extracts were prepared from every second sections and IDUA activity was measuered. Results are shown in FIG. 4. They indicate high enzyme activity at the injection site and in adjacent areas. Enzyme spreading could be demonstrated over 7 slices, which represent a maximal extension of 2.8 cm. Histological analysis is currently performed to assess the extend of disease correction. With respect to the short term follow up of the animal, the limited amount of injected vector and our knowledge that correction extents further than detected enzyme activity, it may be anticipated that four stereotactic injections (two in each hemisphere) might be sufficient for disease correction in the entire dog brain. This hypothesis will be investigated in the next available MPS I dogs. Results from these experiments will help designing a therapeutic protocol in affected children.

In summary, lysosomal storage disease can be corrected through the delivery of the missing enzyme. For those diseases affecting the central nervous system, which are the more frequent ones, intracerebral delivery supposes in situ enzyme secretion. This can be obtained by gene therapy methods. Stereotactic injection of AAV-based vectors encoding the missing enzyme in the brain leads to inducing enzyme secretion in a small number of genetically-modified cells that provide an intra-cerebral source of enzyme. Enzyme can be transported to remote locations leading to the definitive correction of storage lesions in the entire brain. We obtained these results in the mouse model of MPS VII, which is deficient for β-glucuronidase, and now in the MPS I mouse, which is deficient for alpha-L-iduronidase (IDUA) and which provides a model for Hurler's disease, a disorder relatively frequent in children.

Correction in MPS I mice was obtained by using an AAV-2 derived vector (AAV-PKG-IDUA). Expression levels with this vector, and spreading of the activity through out the brain was much more efficient than with previously described AAV vectors. Efficiency seems related in the use of a murine phosphoglycerate promoter (PGK) and the addition of sequences called WPRE for woodchuck hepatitis virus posttranscriptional regulatory element, which are known to increase mRNA stability and traductability.

Though the concept has been widely publicized that a stereotactic injection of an AAV vector is expected to cure lysosomal storage lesions in the brains of mice with mucopolysaccharidosis, these results with the AAV-PGK-IDUA vector provide the first demonstration that this strategy is effective in treating MPS I, which is one of the most attractive clinical targets.

Enzyme activity levels attained in the brain of MPS I mice with the AAV-PGK-IDUA vector were much higher than previously reported with AAV vectors in different models. The volume of brain tissue in which activity was detected, and the volume in which a correction of lesions was observed were much broader than previously reported in different models of affected mice. Expression levels were achieved allowing a therapeutic effect in the entire brain with a single vector injection, which is clinically relevant result, whereas similar achievement required multiple injections in previous reports.

The AAV-PGK-IDUA vector has also recently been used in a canine model of MPS I. We could confirm in dogs the efficient spreading of enzyme activity in the brain following a single intrstriatal vector injection.

Recombinant bacteria containing nucleic acid molecules of the invention have been deposited at the Collection Nationale de Cultures de Microorganismes ("C.N.C.M.") Institute Pasteur, 28, rue du Docteur Roux, 75724 Paris Cedex 15, France, as follows:

| Plasmid | Accession No. | Deposit Date |
|---|---|---|
| AAV2-mPGK-hNaGlu-WPRE-pA | 1-2891 | Jun. 20, 2002 |
| AAV2-mPGK-IDUA-WPRE-pA | 1-2892 | Jun. 20, 2002 |

REFERENCES

The following references are cited herein. The entire disclosure of each reference is relied upon and incorporated by reference herein.

Adra, C. N., Boer, P. H., and McBurney, M. (1987). Cloning and expression of the mouse pgk-1 gene and the nucleotide sequence of its promoter. Gene 60, 65–74.

Barton, N. W., Brady, R. O., Dambrosia, J. M., Di Bisgeglie, A. M., Doppelt, S. H., Hill, S. C., Mankin, H. J., Murray, G. J., Parker, R. I., Argoff, C. E., et al. (1991). Replacement therapy for inherited enzyme deficiency—macrophage-targeted glucocerebrosidase for Gaucher's disease. N Engl J Med 23, 1464–1470.

Birkenmeier, E. H., Davisson, M. T., Beamer, W. G., Ganschow, R. E., Vogler, C. A., Gwynn, B., Lyford, K. A., Maltais, L. M., and Wawrzyniak, C. J. (1989). Murine mucopolysaccharidosis type VII. Characterization of a mouse with b-glucuronidase deficiency. J Clin Invest 83, 1258–1266.

Bosch, A., Perret, E., Desmaris, N., and Heard, J. M. (2000a). Long-term and significant correction of brain lesions in adult mucoploysaccharidosis type VII mice using recombinant AAV vectors. Mol Ther 1, 63–70.

Bosch, A., Perret, E., Desmaris, N., Trono, D., and Heard, J. M. (2000b). Reversal of pathology in the entire brain of mucoploysaccharidosis type VII mice after lentivirus-mediated gene transfer. Human Gene Ther 11, 1139–1150.

Clarke, L. A., Russel, C. S., Pownall, S., Warrington, C. L., Borowski, A., Dimmick, J. E., Toone, J., and Jirik, F. R. (1997). Murine munopolysaccaridosis type I: targeted disruption of the murine alpha-L-liduronidase gene. Human Mol Genet 6, 503–511.

Consiglio, A., Quattrini, A., Martino, S., Bensadoun, J. C., Dolcetta, D., Trojani, A., Benaglia, G., Marchesini, S., Cestari, V., Oliverio, A., et al. (2001). In vivo gene therapy of metachromatic leukodystrophy by lentiviral vectors: correction of neuropahtology and protection agaisnt learning impairments in affected mice. Nature Med 7, 310–316.

Constantopoulos, G., Shull, R. M., Hastings, N., and Neufeld, E. F. (1985). Neurochemical characterization of canine alpha-L-iduronidase deficiency disease. J Neurochemistry 45, 1213–1217.

Daly, T., Okuyama, T., Vogler, C., Haskins, M., Muzyczka, N., and Sands, M. (1999a). Neonatal intramuscular injection with recombinant adeno-associated virus results in prolonged beta-glucuronidase expression in situ and correction of liver pathology in mucopolysaccharidosis type VII mice. Hum Gene Ther 10, 85–94.

Daly, T. M., Vogler, C., Levy, B., Haskins, M. E., and Sands, M. S. (1999b). Neonatal gene transfer leads to widespread correction of pathology in a murine model of lysosomal storage disease. Proc Natl Acad Sci USA 96, 2296–2300.

Eng, C. M., Cochat, P., Wilcox, W. R., Germain, D. P., Lee, P., Waldek, S., Caplan, L., Heymans, H., Braakman, T., Fitzpatrick, M. A., et al. (2000). Enzyme replacement therapy in Fabry disease: results of a placebo-controlled phase 3 trial. Am J Hum Genet 67 (suppl. 2), 38-ABS 134.

Fratantoni, J., Hall, C., and Neufeld, E. (1968). Hurler and Hunter syndromes: mutual correction of the defect in cultured fibroblasts. Science 162, 570–572.

Ghodsi, A., Stein, C., Derksen, T., Yang, G., Anderson, R. D., and Davidson, B. L. (1998). Extensive β-glucuronidase activity in murine central nervous system after adenovirus-mediated gene transfer to brain. Huamn Gene Ther 9, 2331–2340.

Goodwin, E., and Rottman, F. (1992). The 3' flanking sequence of the bovine growth hormone gene contains novel elements required for efficient and accurate polyadenylation. J Biol Chem 267, 16330–16334.

Grabowski, G. A., Leslie, N., and Wenstrup, R. (1998). Enzyme therapy for Gaucher disease: the first 5 years. Blood Rev 12, 115–133.

Hess, B., Saftig, P., Hartmann, D., Coenen, R., Lullmann-Rauch, R., Goebel, H. H., Evers, M., von Figura, K., D'Hooge, R., Nagels, G., et al. (1996). Phenotype of arylsulfatase A-deficient mice: relationship to human metachromatic leukodystrophy. Proc Natl Acad Sci USA 93, 14821–14826.

Kakkis, E. D., MaEntee, M. F., Schmidtchen, A., Neufeld, E. F., Ward, D. A., Gompf, R. E., Kania, S., Bedolla, C., Chien, S. L., and Shull, R. (1996). Long-term and high-dose trials of enzyme replacement therapy in the canine model of mucopolysaccharidosis I. Biochemical and Mol Med 58, 156–167.

Kaplan, A., Achord, D. T., and Sly, W. S. (1977). Phosphohexosyl components of a lysosomal enzyme are recognized by pinocytosis receptors on human fibroblasts. Proc Natl Acad Sci USA 74, 2026–2030.

Kardower, J. H., Emborg, M. E., Bloch, J., Ma, S. Y., Chu, Y., Leventhal, L., McBride, J., Chen, E. Y., Palfi, S., Roitberg, B. Z., et al. (2000). Neurodegeneration prevented by lentiviral vector delivery of GDNF in primate models of Parkinson's disease. Science 290, 767–773.

Li, H. H., Yu, W. H., Rozengurt, N., Zhao, H. Z., Lyons, K. M., Anagnostaras, S., Fanselow, M. S., Suzuki, K., Vanier, M. T., and Neufeld, E. F. (1999). Mouse model of Sanfilippo syndroem type B produced by targeted disruption of the gene encoding alpha-N-acetylglucosaminidase. Proc Natl Acad Sci USA 96, 14505–14510.

Lutzko, C., Kruth, S., Abrams-Ogg, A. C. G., Lau, K., Li, L., Clark, B. R., Ruedy, C., Nanji, S., Foster, R., Kohn, D., et al. (1999). Genetically corrected autologous stem cells engraft, but host immune responses limit their utility in canine alpha-L-iduronidase deficiency. Blood 93, 1895–1905.

Menon, K. P., Tieu, P. T., and Neufeld, E. F. (1992). Architecture of the canine IDUA gene and mutation underlying canine mucopolysaccharidosis I. Genomics 14, 763–768.

Salvetti, A., Moullier, P., Cornet, V., Brooks, D., Danos, O., and Heard, J. M. (1995). In vivo delivery of human a-L-iduronidase in mice implanted with neo-organs. Human Gene Ther 6, 1153–1159.

Salvetti, A., Orève, S., Chadeuf, G., Favre, D., Champion-Arnaud, P., David-Ameline, J., and Moullier, P. (1998). Factors influencing recombinant adeno-associated virus production. Human Gene Ther 9, 695–706.

Samulski, R. J., Chang, L. S., and Shenk, T. (1987). A recombinant plasmid from which an infectious adeno-associated virus genome can be excised in vitro and its use to study viral replication. J Virol 61, 3096–3101.

Sando, G., and Neufeld, E. F. (1977). Recognition and receptor-mediated uptake of a lysosomal enzyme, a-l-iduronidase, by cultured human fibroblasts. Cell 12, 619–627.

Sands, M. S., Vogler, C., Kyle, J. W., Grubb, J. H., Levy, B., Galvin, N., Sly, W. S., and Birkenmeier, E. H. (1994). Enzyme replacement therapy for murine mucopolysaccharidosis type VII. J Clin Invest 93, 2324–2331.

Sands, M. S., Vogler, C., Torrey, A., Levy, B., Gwynn, B., Grubb, J., Sly, W. S., and Birkemeier, E. H. (1997). Murine mucopolysaccharidosis type VII: long term effect of enzyme replacement and enzyme replacement followed by bone marrow transplantation. J Clin Invest 99, 1596–1605.

Schiffmann, R., Kobb, J. B., Austin, H., Moore, D. F., Sabnis, S., Weibel, T., Balow, J. E., and Brady, R. O. (2000). Efficacy and safety of enzyme replacement therapy for Fabry disease demonstrated by a double-blind placebo-controlled trail. Am J Hum Genet 67 (suppl. 2), 38-ABS.135.

Scott, H. S., Anson, D. S., Osborn, A. M., Nelson, P. V., Clements, P. R., Morris, C. P., and Hopwood, J. J. (1991). Human alpha-L-iduronidase: cDNA isolation and expression. Proc Natl Acad Sci USA 88, 9695–9699.

Shull, R. M., Hastings, N. E., Selcer, R. R., Jones, J. B., Smith, J. R., Cullen, W. C., and Constantopoulos, G. (1987). Bone marrow transplantation in canine mucopolysaccharidosis I. J Clin Invest 79, 435–443.

Shull, R. M., Kakkis, E. D., McEntee, M. F., Kania, S. A., Jonas, A. J., and Neufeld, E. F. (1994). Enzyme replacement in a canine model of Hurler syndrome. Proc Natl Acad Sci USA 91, 12937–12941.

Shull, R. M., Munger, R. J., Spellacy, E., Hall, C. W., Constantopoulos, G., and Neufeld, E. (1982). Canine a-L-Iduronidase deficiency: a model of Mucopolysaccharidosis I. Amer J Pathol 109, 244–248.

Skorupa, A. F., Fischer, K. J., Wilson, J. M., Parente, M. K., and Wolfe, J. H. (1999). Sustained production of β-glucuronidase from localized sites after AAV vector gene transfer results in widespread distribution of enzyme and reversal of lysosomal storage lesions in mucoplysaccharidosis VII mice. Exp Neurol 160, 17–27.

Snyder, E. Y., Taylor, R. M., and Wolfe, J. H. (1995). Neural progenitor cell engraftment corrects lysosomal storage throughout the MPS VII mouse brain. Nature 374, 367–370.

Spellacy, E., Shull, R. M., Canstantopoulos, G., and Neufled, E. F. (1983). A canine model of human alpha-L-iduronidase deficiency. Proc Natl Acad Sci USA 80, 6091–6095.

Stein, C., Ghodsi, A., Derksen, T., and Davidson, B. (1999). Systemic and central nervous system correction of lysosomal storage in mucopolysaccharidosis type VII mice. J Virol 73, 3424–3429.

Taylor, R. M., and Wolfe, J. H. (1997). Decreased lysosomal storage in the adult MPS VII mouse brain in the vicinity of grafts of retroviral-corrected fibroblasts secreting high levels of β-glucuronidase. Nature Med 3, 771–774.

van der Hout, H., Reuser, A., Vulto, A., Arts, W. F., Cromme-Dijkhuis, A., Hop, W., and van der Ploeg, A. (2000). First clinical test with recombinant human alpha-glucosidase from rabbit milk shows therapeutic effect in Pompe patients. Amer J Hum Genet 67 (suppl. 2), 10-ABST.16.

Vogler, C., Sands, M., Higgins, A., Levy, B., Grubb, J., Birkenmeier, E. H., and Sly, W. S. (1993). Enzyme replacement with recombinant β-glucuronidase in the newborn mucopolysaccharidosis type VII mouse. Pediatr Res 34, 837–840.

Vogler, C., Sands, M. S., Levy, B., Galvin, N., Birkenmeier, E. H., and Sly, W. S. (1996). Enzyme replacement with recombinant beta-glucuronidase in murine mucopolysaccharidosis type VII: impact of therapy during the first six weeks of life on subsequent lysosomal storage, growth, and survival. Pediatr Res 39, 1050–1054.

Walkley, S. U., Haskins, M. E., and Shull, R. (1988). Alterations in neuron morphology in mucopolysaccharidosis type I. Acta Neuropathol 75, 611–620.

Zhao, H. G., Li, H. H., Schidthen, A., and Neufeld, E. F. (1996). The molecular basis of Sanfilippo syndrome type B. Proc Natl Acad Sci USA 93, 6101–6105.

Zufferey, R., Donello, J. E., Trono, D., and Hope, T. J. (1999). Woodchuck hepatitis virus posttranscriptional regulatory element enhances expression of transgenes delivered by retroviral vectors. J Virol 73, 2886–2892.

|      |            |            |            |            |            |            |            |            |            |            |
|------|------------|------------|------------|------------|------------|------------|------------|------------|------------|------------|
|      | \| 10      | \| 20      | \| 30      | \| 40      | \| 50      | \| 60      | \| 70      | \| 80      | \| 90      | \| 100     |
| 1    | CAGCAGCTGC | GCGCTCGCTC | GCTCACTGAG | GCCGCCCGGG | CAAAGCCCGG | GCGTCGGGCG | ACCTTTGGTC | GCCCGGCCTC | AGTGAGCGAG | CGAGCGCGCA |
| 101  | GAGAGGGAGT | GGCCAACTCC | ATCACTAGGG | GTTCCTTGTA | GTTAATGATT | AACCCGCCAT | GCTACTTATC | TACTCGAGAA | TTCTACCGGG | TAGGGAGGC  |
| 201  | GCTTTTCCCA | AGGCAGTCTG | GAGCATGCGC | TTTAGCAGCC | CCGCTGGCAC | TTGGCCTCTA | ACAAGTGGCC | TCTGGCCTCG | CACACATTCC | ACATCCACCG |
| 301  | GTAGCGCCAA | CCGGCTCCGT | TCTTTGGTGG | CCCCTTCCG  | CCACCTTCTA | CTCCTCCCCT | AGTCAGGAAG | TTCCCCCCGC | GCGGGTAGGC | GCGTCGTGCA |
| 401  | GGACGTGACA | AATGGAAGTA | GCACGTCTCA | CTAGTCTCGT | GCAGATGGAC | AGCACCGCTG | AGCAATGGAA | GCGGGCAGCA | CTTTGGGGCA | GCGGCCAATA |
| 501  | GCAGCTTTGC | TCCTTCGCTT | TCTGGGCTCA | GAGGCTGGA  | AGGGGTGGGT | CCGGGGGCGG | GCTCAGGGGC | GGGCTCAGGG | CCGGGGCCGG | CCGAAGGTC  |
| 601  | CTCCCGGAGCC | CGGCATTCTG | CACGCTTCAA | AAGCGCACGT | CTGCCGCGCT | GTTCTCCTCT | TCCTCATCTC | GACCGGATCA | GATCGAATTC |            |
| 701  | CCCGAAGCC  | CGCAGTCCCC | GAGCACGCGT | GGCCATGCCT | CCCCTGCCCC | CCCGCCCCGC | GCTGCTGGCG | CTCCTCTGCC | CGTCCTCTGC | CCGCCCCCG  |
| 801  | GTGGCCCCGG | CCGAGGCCCC | GCACCTGGTG | GCACCTGGTG | CATGTGGACG | ACTGGGACTC | CCCTGTGGCC | CTGTGGCGCT | CACAGGCTTC | TGCCCCCCGC |
| 901  | TGCCACACAG | CCAGGCTGAC | CAGTACGTCC | TCAGCTGGGA | AACCTCGCCT | AACCTCGCCT | ATGTGGGCGC | CGTCCCTCAC | CACCTGGACG | AGCAGGTCCG |
| 1001 | GACCCACTGG | CTGCTGGAGC | TTGTCACCAC | CAGGGGGTCC | ACTGGACGGG | GCCTAGCTA  | CAACTTCACC | GGTACTGGA  | CCTTCTCAGG |            |
| 1101 | GAGAACCAGC | TCCTCCCAGG | GTTTGAGCTG | ATGGGCAGCG | CCTCGGGCCA | CTTTCACTGAC | TTTGAGGACA | AGCAGGTGTT | TGAGTGGAAG | GACTTGGTCT |
| 1201 | CCAGCCTGGC | CGCAGCATCA | ACGACGAGGC | GAACCTGCTA | CTGGCCAACA | AAGTGTTTCC | TCGAGACGTG | GAATGAGCCA | GACCACCACG | ACTTTGACAA |
| 1301 | CGTTCTCCATG | CGGCTCAGCC | ATCGGTAGGT | GCTTCCTGAA | CTACTACGAT | GCCTGCTCGG | AGGGTCTGCC | CGCCCCCAGC | GGCTGGGAGG | CCCCGGGAC  |
| 1401 | TCCTTCCACA | CCCCACCGCG | ATCCCCGCTG | AGTGGGGCC  | CTGCCGCCA  | CTGCCACGAC | GGTACCAAC  | TCTTCACTGG | CGCAGAGATC | CGGCAGCTCT |
| 1501 | ACTACATCTC | CCTCCACAGG | AAGGGTGCGC | GCAGCTCCAT | CTCCATCCTG | GACCAGGAGA | AGGTCTCGC  | GCAGCAGATC | CGGCACGTGA | TCCCCAAGTT |
| 1601 | CGGCGACACC | CCCATTTACA | ACGACGAGGC | GGACCCGCTG | GTGGGCTGGT | CCCTGCCACA | GCCGTGGAGG | GCGACGTGA  | CCTACGCGGC | CATGGTGGTG |
| 1701 | AAGGTCATCG | CGCAGCTGCTA | GAACCTGCTA | CTGCCCAACA | CCACCTCCGC | CTTCCCCGC  | GCGCTCCTGA | GCAACGACAA | TGCCTTCCTG | AGCTACCACC |
| 1801 | CGCAGCCCCTT | CGGCCAGCGC | ACGCTCACCG | CGGCTTCCA  | GGTCAACAAC | ACCCCCCCGC | AGGCCCGGAC | GCTGTTGCGC | AAGCCGGTGT | TCACGGCCAT |
| 1901 | CGGGCCGTG | GCGCTCTGTG | ATGAGGAGCA | GCTCTGGCCG | GCCCTGGGCG | GAAGTGCGA  | CGTCCTGAC  | AGGCCGGAGC | CGTGTTGCCC | CCTGGCCAGC |
| 2001 | GCCCCACCGG | CCCCACCGCC | GGCCGACGCC | TGGCGCGCCG | CGGCCGACGC | CTACGGCGAG | CGGACACCC  | GCCGCCACCC | CAACCGCGAG | GTGCGGGTGG |
| 2101 | CCCTGCGCGT | GCGGGGGTG  | CCCCCGGGGC | CGGCAGAGCA | GTTCCGGGCC | CTGAGGACCC | CTGAGGACCC | ACAACGGGCT | CTGCAGCCCC | GACGGCGAGT | GGCGGGCCT |
| 2201 | GGGCCCGGCC | GTCTTCCCCA | CGGCAGAGCA | GTTCCGGGCC | ATGCGGCCGC | CTGAGGACCC | CCGAGAAGC  | GGTGGCCGCG | CCTTACCCGC | CGGCGGCCGC |
| 2301 | CTGACCCGTG | GCGCCCTGCC | GCGGCTGCCG | TCGCTTTTGC | TGGTGCACGT | GTGTGCCAGT | CCCGAGAAGC | GGTCACGCGG | GGTCACGCGG | CTCCGCCCC  |
| 2401 | TGCCCCTGAC | CCAAGGGCAG | CTGGTTCTGG | TCTGTTCGGA | GGCTCCAAGT | GGCTCCAAGT | GCCTCGTGAC | ATACGAGATC | CAGTTCTCTC | AGGACGGTAA |
| 2501 | GGCGTACACC | CCCGGTCAGCA | GGAAGCCATC | GACCTTCAAC | CTCTTTGTGT | TCAGCCCAGA | CACAGGTGCT | GTCTCTGGCT | CCTACCGAGT | TCGAGCCCTG |

| | | | | | | | |
|---|---|---|---|---|---|---|---|
| 2601 | GACTACTGGG | CCCGACCAGG | CCCCTTCTCG | GACCCTGTGC | CGTACCTGGA | GGTCCCTGTG | CCAAGAGGGC | CCCCATCCCC | GGGCAATCCA | TGAGCCTGTG | 2700 |
| 2701 | CTGAGCCCCA | GTGGGTTGGC | GATTAGTCCA | ATTTGTTAAA | GACAGGATAT | CAGTGTCCA | GGCTCTAGTT | TTGACTCAAC | AATATCACCA | GCTGAAGCCT | 2800 |
| 2801 | ATAGAGTACG | AGCCATAGAT | AAAATAAAAG | ATTTTATTTA | GTCTCCAGAA | AAAGGGGGA | ATGAAAGACC | CCACCTGTAG | GTTTGGCAAG | CTAGtCTAGT | 2900 |
| 2901 | AACGGCCGCC | AGTGTGCTGG | AATTCTGCAG | ATATCCATCA | CACTGGCGGC | CGCTCCAGCA | TGCATCTAGA | Gcgataatca | acctctggat | tacaaaattt | 3000 |
| 3001 | gtgaagatt | gactgtatt | cttaactatg | ttgctccttt | tacgctatgt | ggatacgctg | ctttaatgcc | tttgtatcat | gctattgctt | cccgtatggc | 3100 |
| 3101 | tttcattttc | tcctccttgt | ataaatcctg | gttgctgtct | ctttatgagg | agttgtgcc | cgttgtcagg | caacgtggcg | tggtgtgcac | tgtgtttgct | 3200 |
| 3201 | gacgcaaccc | ccactggttg | gggcattgcc | accacctgtc | agtccttttc | cgggacttc | gccttcccc | tccctatggc | cacggcggaa | ctcatcgccg | 3300 |
| 3301 | cctgccttgc | ccgctgctgg | acaggggctc | ggctgttggg | cactgacaat | tccgtgtgtt | tgtcgggggaa | gctgacgtcc | tttccatggc | tgctcgcctg | 3400 |
| 3401 | tgttgccacc | tggattctgc | gcgggacgtc | cttctgctac | gtccccatcc | agcggacctt | ccttcccgcg | gctgctgcc | ggctctgcgg | 3500 |
| 3501 | cctcttccgc | gtcttgacct | tcgccctgag | acgagtcgga | tctcccttg | ggccgcctcc | ccgcatcgCT | ATTCTATAGT | GTCACCTAAA | TGCTAGAGCT | 3600 |
| 3601 | CGCTGATCAG | CCTCGACTGT | GCCTTCTAGT | TGCCAGCCAT | ATTGCATCGC | ATTGTCTGAG | CCCCTTCCT | GTGCCTTCCT | TGACCCTGGA | AGTGCCACT | CCCACTGTCC | 3700 |
| 3701 | TTTCCTAATA | AAATGAGGAA | AGGCATGCTG | GGGATGCGGT | TTGTGCTCAT | TAGGTGTCAT | TCTATTCTGG | GGGGTGGGGT | CAGTGAGGAC | AGCAAGGGGG | AGGATTGGA | 3800 |
| 3801 | AGACAATAGC | AGGCATGCTC | GGGATGCGCT | CCTCTCTCCG | GCTTCTGAGG | CGGAAAGAAC | CAGTAGATA | AGTAGCATGG | CGGGTTAATC | ATTAACTACA | 3900 |
| 3901 | AGGAACCCCT | AGTGATGGAG | TTAAGCGCGG | TTGGCCACTC | CCTCTCTCCG | CTCACTGAGG | CTACACTTGC | CAGCGCCCTA | GCGCCCGCTC | CTTTCGCTTT | 4000 |
| 4001 | GGCGGGCCTCA | GTGAGCGAGC | GAGCGCGCAG | CTGGCGTAAT | AGCGAAGAGG | CCCGCACCGA | TCGCCCTTCC | CAACAGTTGC | GCAGCCTGAA | TGGCGAATGG | 4100 |
| 4101 | CGATTCCGTT | GCAATGGCTG | GCGGTAATAT | TGTTCTGGAT | ATTACCAGCA | AGGCCCATAG | TTTGAGTTCT | TCTACTCAGG | CAAGTGATGT | TATTACTAAT | 4200 |
| 4201 | CAAAGAAGTA | TTGCGACAAC | GGTTAATTTG | CGTGATGGAC | AGACTCTTTT | ACTCGGTGGC | CTCCCGCTCT | GATTCTAACG | AGGAAAGCAC | GTTATACGTG | TCTCAGGAT | CAACCATAGT | 4300 |
| 4301 | CGTTCCTGTC | TAAAATCCCT | TTAATCGGCC | TCCTGTTTAG | CTCCCGCTCT | GATTCTAACG | AGGAAAGCAC | GTTATACGTG | CTCGTCAAAG | CTTTTCTGA | 4400 |
| 4401 | ACGCGCCCTG | TAGCGGCGCA | TTAAGCGCGG | CGGGTGTGGT | GGTTACGCGC | AGCGTGACCG | CTACACTTGC | CAGCGCCCTA | GCGCCCGCTC | CTTTCGCTTT | 4500 |
| 4501 | CTTCCCTTCC | TTTCTCGCCA | CGTTCGCCGG | CTTTCCCCGT | CAAGCTCTAA | ATCGGGGGCT | CCCTTTAGGG | TTCCGATTTA | GTGCTTTACG | GCACCTCGAC | 4600 |
| 4601 | CCCAAAAAAC | TTGATTAGGG | TGATGGTTCA | CGTAGTGGGC | CATCGCCCTG | ATAGACGGTT | TTTCGCCCTT | TGACGTTGGA | GTCCACGTTC | TTTAATAGTG | 4700 |
| 4701 | GACTCTTGTT | CCAAACTGGA | ACAACACTCA | ACCCTATCTC | GGTCTATTCT | TTTGATTTAT | AAGGGATTTT | GCCGATTTCG | GCCTATTGGT | TAAAAAATGA | 4800 |
| 4801 | GCTGATTTAA | CAAAAATTTA | ACGCGAATTT | TAACAAAATA | TTAACGCTTA | CAATTTAAAT | ATTTGCTTAT | ACAATCTTCC | TGTTTTTGGG | GCTTTTCTGA | 4900 |
| 4901 | TTATCAACCG | GGGTACATAT | GATTGACATG | CTAGTTTTAC | GATTACCGTT | CATCGATTCT | CTTGTTTGCT | CCAGACTCTC | AGGCAATGAC | CTGATAGCCT | 5000 |
| 5001 | TTGTAGAGAC | CTCTCAAAAA | TAGCTACCCT | CTCCGGCATG | AATTTATCAG | CTAGAACGGT | TGAATATCAT | ATTGATGGTG | ATTTGACTGT | CTCCGGCCTT | 5100 |
| 5101 | TCTCACCCGT | TTGAATCTTT | ACCTACACAT | TACTCAGGCA | TTGCATTTAA | AATATATGAG | GGTTCTAAAA | ATTTTTATCC | TTGCGTTGAA | ATAAAGGCTT | 5200 |
| 5201 | CTCCCCGCAAA | AGTATTACAG | GGTCATAATG | TTTTTGGTAC | GCTTTATGCT | CTGAGGCTTT | ATTGCTTAAT | TTTGCTAATT | CTTTGCCTTG | 5300 |

```
5301  CCTGTATGAT TTATTGGATG TTGGAAATCGC CTGATGCCGT ATTTTCTCCT TACGCATCTG TGCGGTATTT CACACCGGCAT ATGGTGCACT CTCAGTACAA  5400
5401  TCTGCTCTGA TGCCGCATAG TTAAGCCAGC CCCGACACCC GCCAACACCC GCTGACGGGC CCTGACGCGC TTGTCTGCTC CCCGCATCCG CTTACAGACA  5500
5501  AGCTGTGACC GTCTCCGGGA GCTCCATGTG TCACCGTCAT CACCGAAACG CGCCGAGACGA AAGGCCCTCG TGATACGCCT ATTTTTATAG         5600
5601  GTTAATGTCA TGATAATAAT GGTTTCTTAG ACGTCAGGTG GCACTTTTCG GGGAAATGTG CGCGGAACCC CTATTTGTTT ATTTTTCTAA ATACATTCAA  5700
5701  ATATGTATCC GCTCATGAGA CAATAAACCT GATAAATGCT TCAATAATAT TGAAAAAGGA AGAGTATGAG TATTCAACAT TTCCGTGTCG CCCTTATTCC  5800
5801  CTTTTTTGCG GCATTTTGCC TTCCTGTTTT TGCTCACCCA GAAACGCTGG TGAAAGTAAA AGATGCTGAA GATCAGTTGG GTGCACGAGT GGGTTACATC  5900
5901  GAACTGGATC TCAACAGCGG TAAGATCCTT GAGAGTTTTC GCCCCGAAGA ACGTTTTCCA ATGATGAGCA CTTTTAAAGT TCTGCTATGT GGCGCGGTAT  6000
6001  TATCCCGTAT TGACGCCGGG CAAGAGCAAC TCGGTCGCCG CATACACTAT TCTCAGAATG ACTTGGTTGA GTACTCACCA GTCACAGAAA AGCATCTTAC  6100
6101  GGATGGCATG ACAGTAAGAG AATTATGCAG TGCTGCCATA ACCATGAGTG GCCAACTTA CTTCTGACAA CATCGGGAGG ACCGAAGGAG             6200
6201  CTAACCGCTT TTTTGCACAA CATGGGGGAT CATGTAACTC GCCTTGATCG TTGGGAACCG GAGCTGAATG AAGCCATACC AAACGACGAG CGTGACACCA  6300
6301  CGATGCCTGT AGCAATGGCA ACAACGTTGC GCAAACTATT AACTGGCGAA CTACTTACTC TAGCTTCCCG GCAACAATTA ATAGACTGGA TGGAGGCGGA  6400
6401  TAAAGTTGCA GGACCACTTC TGCGCTCGGC CCTTCCGGCT ATCGTAGTTA TCTACACGAC GGGGAGTCAG GCAACTATGG GGTCTCGCGG TATCATTGCA  6500
6501  GCACTGGGGC CAGATGGTAA GCCCTCCCGT ATCCTAGTTA TCTACACGAC GGGGAGTCAG GCAACTATGG ATGAACGAAA TAGACAGATC GCTGAGATAG  6600
6601  GTGCCTCACT GATTAAGCAT TGGTAACTGT CAGACCAAGT TTACTCATAT ATACTTTAGA TTGATTTAAA ACTTCATTTT TAATTTAAAA GGATCTAGGT  6700
6701  GAAGATCCTT TTTGATAATC TCATCGACCA AATCCCTTAA CGTGAGTTTT CGTTCCACTG AGCGTCAGAC CCCGTAGAAA AGATCAAAGG ATCTTCTTGA  6800
6801  GATCCTTTTT TTCTGCGCGT AATCTGCTGC TTGCAAACAA AAAAACCACC GCTACCAGCG GTGGTTTGTT TGCCGGATCA GAGCTACCA ACTCTTTTTC  6900
6901  CGAAGGTAAC TGGCTTCAGC AGAGCGCAGA TACCAAATAC TGTTCTTCTA GTGTAGCCGT AGTTAGGCCA CCACTTCAAG AACTCTGTAG CACCGCCTAC  7000
7001  ATACCTCGCT CTGCTAATCC TGTTACCAGT GGCTGCTGCC AGTGGCGATA AGTCGTGTCT TACCGGGTTG GACTCAAGAC GATAGTTACC GGATAAGGCG  7100
7101  CAGCGGTCGG GCTGAACGGG GGGTTCGTGC ACACAGCCCA GCTTGGAGCG AACGACCTAC ACCGAACTGA GATACCTACA GCGTGAGCTA TGAGAAAGCG  7200
7201  CCACGCTTCC CGAAGGGAGA AAGGCGGACA GGTATCCGGT AAGCGGCAGG GTCGGAACAG GAGAGCGCAC GAGGGAGCTT CCAGGGGGAA ACGCCTGGTA  7300
7301  TCTTTATAGT CCTGTCGGGT TTCGCCACCT CTGACTTGAG CGTCGATTTT TGTGATGCTC GTCAGGGGGG CGGAGCCTAT GGAAAAACGC CAGCAACGCG  7400
7401  GCCTTTTTAC GGTTCCTGGC CTTTTGCTGG CCTTTTGCTC ACATGTTCTT TCCTGCGTTA TCCCCTGATT CTGTGGATAA CCGTATTACC GCCTTTGAGT  7500
7501  GAGCTGATAC CGCTCGCCGC AGCCGAACGA CCGAGCGCAG CGAGTCAGTG AGCGAGGAAG CGGAAGAGCG CCCAATACGC AAACCGCCTC TCCCCGCGCG  7600
7601  TTGGCCGATT CATTAATGCA GCTGCGCGCT CGCTCGCTCA CTGAGGCC                                                         7648
   1  CAGCAGCTGC GCGCTCGCTC GCTCACTGAG GCCGCCCGGG CAAAGCCCGG GCGTCGGGCG ACCTTTGGTC GCCCGGCCTC AGTGAGCGAG CGAGCGCGCA  100
 101  GAGAGGGAGT GGCCAACTCC ATCACTAGGG GTTCCTTGTA GTTAATGATT AACCCGCCAT GCTACTATC TACTCGAGAA TTCTACCGGG TAGGGAGGC  200
         |          |          |          |          |          |          |          |          |          |
        10         20         30         40         50         60         70         80         90        100
```

| | | | | | | | | |
|---|---|---|---|---|---|---|---|---|
| 201 | GCTTTTCCCA | AGGCAGTCTG | GAGCAGTGCC | TTTAGCAGCC | CCGCTGGCAC | ACAAGTGGCC | TCTGCCTCG | CACACATTCC | ACATCACCG 300 |
| 301 | GTAGCGCCAA | CCGGCTCCGT | TCTTTGGTGG | CCCCTTCGCG | CTCCTCCCT | AGTCAGGAAG | TTCCCCCGC | CCCGCAGCTC | GCGTCGTGCA 400 |
| 401 | GGACGTGACA | AATGGAAGTA | GCACGTCTCA | CTAGTCTCGT | GCAGATGGAC | AGCAATGGAA | GCGGTAGGC | CTTTGGGCA | GCGGCAATA 500 |
| 501 | GCAGCTTTGC | TCCTTCGCTT | TCTGGGCTCA | GAGGCTGGGA | AGGGGTGGGT | CCGGGGGGAG | GGCTCAGGGG | GCGGGGGG | CGGAAGGTC 600 |
| 601 | CTCCGGAGCC | CGGCATTCTG | CACGCTTCAA | AAGCGCACGT | CTGCCGCGCT | GTTCTCCTCT | TCCTCATCTC | CGGGCCTTTC | CCCGGCTGC 700 |
| 701 | AGGAAATTCCG | AGACCATGGA | GGCGGTGGCC | GTGCCGCGG | CCGTGGGGGT | CCTTTCCCTG | GCCGGGGCCC | AGGCGACAG | GCCGGGAGG 900 |
| 801 | CGGGGGCCGT | GCGGGGCCTC | GTGGGCGCGC | TGCTGGGGCC | AGGCCCCGCG | GCCGACTTCT | CCGTGTCGGT | GGAGCGCGCT | CTGGCTGCCA AGCCGGCTT 800 |
| 901 | GGACACCTAC | AGCCTGGGCG | GCGGGCGCCG | CGGGGTGCG | GCCTCCACGG | GGCTCCACAG | CGTGCGGCGG | GCCCCGGGC | CCTGCCGAC 1000 |
| 1001 | TTCTGTGGCT | GCCACGTGGC | CTGTCCCGC | TCTCAGCTGC | GCCTGCCGCG | GCCACTGCCA | GCCGTGCCGG | GGAGCTGAC | CCCAACAGGT 1100 |
| 1101 | ACCGCTATTA | CCAGAATGTG | TGCACGCAA | GCTACTCCTT | CGTGTGGTGG | GACTGGGCCC | GCTGGGAGCG | AGAGATAGAC | TGGAATGGCAT 1200 |
| 1201 | CAACCTGGCA | CTGGCCTGGA | GGCCATGGG | CAGCCGGGCT | ACCTGCTGAC | CCCCCTGCCC | GGGCCTGGCTT | CAGGCAGAGA | TCAATGAGTT CTTTACTGT 1300 |
| 1301 | CCTGCCTTCC | TGGCCTGGGG | GCGAATGGGC | AACCTGCACA | CCTGGGATGG | CAGCGGGTGT | ACCTGCTGGC | CCCTCCTGGC | ACATCAAGCA GCTTTACCTG CAGCACCGGG 1400 |
| 1401 | TCCTGACCA | GATGCCTCC | CCCCAGTGCT | TTCGCATTC | GCGGGCATG | GCCTGCATGC | TTCCCGAGGC | TGTCACCAGG | GTGTTCCCTC AGGTCAATGT 1500 |
| 1501 | CACGTTGGCT | GGCAGTGGGG | GCCACTTAA | CTGTCCCTAC | TTCCTGCTCCT | GCGGGCATG | TCCGGAAGAC | TCCCGAAGGA | GAGCCTCTTC 1600 |
| 1601 | CTGCGAGAGC | TGATCAAAGA | GTTTGGCACA | GACCACATCT | ATGGGGGCCGA | CACTTTCAAT | GAGATGCAGC | CCATATTCCT | TACCTTGCCG 1700 |
| 1701 | CAGCCACCAC | TGCCGTCTAT | GAGGCCATGA | CTGCAGTGGA | TACTGAGGCT | GTGTGCTGC | TCCAAGGCTG | GTCTCTTCCA | AGAGCCCCGC AGTTCTGGGG 1800 |
| 1801 | CTACGTGTA | CTGGCCTGGA | ATCAGGGCTG | TGCTGGGAGC | TGTGCCCCGT | GGTTCTCGGA | CCTGTTTGCT | GGGCCGCCAGC | CTGTGTATAC CCGACTGCC 1900 |
| 1901 | GCCCAGCCAG | ATCGGGCCCT | TTCCCCCTT | CATCGGTGTC | ATGCTGCACA | ACTTTGGGG | AAACCATGGT | CTTTTTGGAG | CCCTAGAGGC GGCCCAGAAG 2000 |
| 2001 | CTGCCCCCT | CTTCCCCAAC | TCCACCATGG | TAGCCACGGG | CTGCCGGAGG | CATGCCCCCC | GAGGAACGA | GCCAGAAGCG | AGTGGTCTAT CTGAGCTGGG 2100 |
| 2101 | CTGGCGGAAAG | GACCCAGTGC | CAGATTTGGC | GCTCCGGCA | CTGGACAGAG | CCAGCCATCA | CCGCCCGGCCG | GTATGGGGTC | TCCACCCCG AGCAGCAGGG 2200 |
| 2201 | CTACTGCTCC | GGAGTGTGTA | CAACTGCTCC | GGGGAGGCCT | GCAGGGGCCA | CAATCGTAGC | CCGCTGGTCA | GGCGCCGTC | CCTACAGATG AATACCAGCA 2300 |
| 2301 | TCTGGTACAA | CCGATCTGAT | GTGTTTGAG | CCTGCGGCT | GCTGCTCACA | TATGAGGAGG | TCTGCTCCCT | CAAGAAGCTG | TTCCGCTACG ACCTGCTGGA 2400 |
| 2401 | CCTCACTCGG | CAGGCAGTGC | AGGAGCTGGT | CAGCTTGTAC | AGGAGCCGC | CTACCTGGCT | TGACAGCCAG | AAGAAGCTG | CCTCCCTGTT GAGGGCTGGA 2500 |
| 2501 | GGCGTCCTGG | CCTATGAGCT | GCTGCCGGCA | CTGGACGAGG | TGCTGGCTAG | TGACAGCCC | TTCTTGCTGG | GCAGCCGCC | CGAGCAGCGG 2600 |
| 2601 | CAGTCAGTGA | GGCCGAGGCC | GATTTCTACG | AGCAGAACAG | CCGCTACCAG | TGACCTTGT | GGGGGCCAGA | AGGCAACATC | CTGGACTATG CCAACAAGCA 2700 |
| 2701 | GCTGGGGGG | TTGGTGGCCA | ACTACTACAC | CCCTCGCTGG | CGGCTTTTCC | TGGAGGCGCT | GGTTGACAGT | GTGCCCCAGG | GCATCCCTTT CCAACAGCAC 2800 |
| 2801 | CAGTTTGACA | AAATGTCTT | CCAACTGGAG | CAGGCCCTTC | TTCTCAGCAA | GCAGAGGTAC | CCCAGCCAGC | CGGAGGAGA | CACTGTGGAC CTGGCCAAGA 2900 |

| | | | | | | |
|---|---|---|---|---|---|---|
| 2901 | AGATCTTCCT | CAAATATTAC | CCCGGCTGGG | TGGCCGGCTC | TTGGTGATAG | ATTCGCCACC | ACTGGGCCTT | GTTTTCCGCT | AATTCCAGGG | CAGATTCCAG | 3000 |
| 3001 | GGCCCAGAGC | TGGACAGACA | TCACAGGATA | ACCCAGGCCT | GGGAGGAGGC | CCCACGGCCT | GCTGGTGGGG | TCTGACCTGG | GGGGATTGGA | GGGAAATGAC | 3100 |
| 3101 | CTGCCCTCCA | CCACCACCCA | AGTGTGGGA | TTAAAGTAGC | TTGGTACCGA | GCTCGGATCC | GGCGATTAGT | CCAATTGTT | AAAGACAGGA | TATCAGTGGT | 3200 |
| 3201 | CCAGGCTCTA | GTTTTGACTC | AACATATCA | CCAGCTGAAG | CCTATAGAGT | ACGAGCCATA | GATAAAATAA | AAGATTTTAT | TTAGTCTCCA | GAAAAGGGG | 3300 |
| 3301 | GGAATGAAAG | ACCCCACCTG | TAGGTTTGGC | AAGCTAGCgc | CTGGAATTCT | GCAGATATCC | ATCACACTGG | CGGCCGCTCG | 3400 |
| 3401 | AGCATGCATC | TAGAGcgata | atcaactct | ggattacaaa | atttgtgaaa | gattgactgg | tattcttaac | tatgttgctc | cttttacgct | atgtggatac | 3500 |
| 3501 | gctgctttaa | tgccttgta | tcatgctatt | gcttcccgta | tggctttcat | tttctcctcc | ttgtataaat | cctggtttgt | gtctctttat | gaggagttgt | 3600 |
| 3601 | ggcccgttgt | caggcaacgt | ggcgtggtgt | gcactgtgtt | tgctgacgca | acccccactg | gttgggcat | tgccaccac | tgcagtcc | tttccgggac | 3700 |
| 3701 | tttcgcttt | ccctccccta | ttgcacggc | ggaactcatc | gccgcctgcc | ttgccaaggg | gctcagtcgt | tgggcactga | caattccgtg | 3800 |
| 3801 | gtgttgcgg | ggaagctgac | gtccttcca | tggctgctcg | cctgtgttgc | cacctgatt | ctgccggga | cgtccgtctg | ctacgtcct | tcggcctca | 3900 |
| 3901 | atccagcgga | ccttcttcc | cgcagcctgc | tgccggctct | gcggcctctt | gccttcgcc | tgagacgagt | cggatctccc | tttgggcgc | 4000 |
| 4001 | ctcccccgcat | cgCTATTCTA | TAGTGTCACC | TAAATGCTAG | AGCTCGCTGA | CTGTGCCTTC | CCATCTGTTG | TTTGCCCCTC | 4100 |
| 4101 | TCCTTGCCCT | TGCCCT | GGGTGGGGTG | GGAAGGTGC | CACTCCCACT | GTCCTTCCT | AATAAAATGA | TCGCATTGCA | GGAAATGATA | TCATTCTATT | 4200 |
| 4201 | CTGGGGGGTG | GGGTGGGGCA | GGACAGCAAG | GGGAGGAGATT | TAGCAGGCAT | GCTGGGGATG | GGTTGGCC | ACTCCCTCTC | TGCCGCTCG | GAGGCGAAA | 4300 |
| 4301 | GAACCAGTA | GATAAGTAGC | ATGGCGGGTT | AATCATTAAC | TACAAGGAAC | CCCTAGTGAT | GGAGTTGCC | CACTCCCTGT | TGCCGCTCG | CTCGCTCACT | 4400 |
| 4401 | GAGGCCGGGC | GACCAAAGGT | CGCCCGACGC | CCGGGCTTTG | CGGGGCGGC | GAGCAGCGC | GCAGCTGGGCG | TAATAGCGAA | GAGGCCCGCA | 4500 |
| 4501 | CCGATCGCCC | TTCCCAACAG | TTGCGCAGCC | TGAATGGCGA | ATGGCGATTC | CGTTGCAATG | GCTGGCGGTA | ATATTGTTCT | GGATATTACC | AGCAAGGCCG | 4600 |
| 4601 | ATAGTTTGAG | TTCTTCTACT | CAGGCAAGTG | ATGTTATTAC | TAATCAAAGA | AGTATTGCGA | CAACGTTAA | CCCTTTAATC | TTTGCGTGAT | GGACAGACTC | TTTTACTCGG | 4700 |
| 4701 | TGGCCTCACT | GATTATAAAA | ACACTTCTCA | GGATTCTGGC | GTACCGTTCC | TGTCTAAAAT | CCCTTTAATC | GGCCTCCTGT | TTAGCTCCCG | CTCTGATTCT | 4800 |
| 4801 | AACGAGGAA | GCACGTTATA | CGTGCTCGTC | AAAGCAACCA | TAGTACGCGC | CCTGTAGCGG | CGCATTAAGC | GCGGCGGGTG | TGGTGGTTAC | GCGCAGCGTG | 4900 |
| 4901 | ACCGCTACAC | TTGCCAGCGC | CCTAGCGCCC | GCTCCTTCG | CTTTCTTCCC | TTCCTTTCTC | GCCACGTTCG | CCGTCAAGCT | CTAAATCGGG | 5000 |
| 5001 | GGCTCCCTTT | AGGGTTCCGA | TTTAGTGCTT | TACGGCACCT | CGACCCCAAA | AACTTGATT | AGGGTGATGG | TTCACGTAGT | GGGCCATCGC | CCTGATAGAC | 5100 |
| 5101 | GGTTTTTCGC | CCTTTGACGT | TGGAGTCCAC | GTTCTTTAAT | AGTGGACTCT | TGTTCCAAAC | TGGAACAACA | CTCAACCCTA | TCTCGGTCTA | TTCTTTTGAT | 5200 |
| 5201 | TTATAAGGGA | TTTTGCCGAT | TTCGGCCTAT | TGGTTAAAAA | ATGAGCTGAT | TTAACGCGA | ATTTTAACAA | AATATTAACG | CTTACAATTT | 5300 |
| 5301 | AAATATTTGC | TTATACAATC | TTCCTGTTTT | TGGGGCTTTT | CTGATTATCA | ACCGGGGTAC | ATATGATTGA | CATGCTAGTT | TTACGATTAC | CGTTCATCGA | 5400 |
| 5401 | TTCTCTTGTT | TGCTCCAGAC | TCTCAGGCAA | TGACCTGATA | GCCTTTGTAG | AGACCTCTCA | AAAATAGCTA | CCCTCTCCGG | CATGAATTTA | TCAGCTAGAA | 5500 |

-continued

```
5501 CGGTTGAATA TCATATTGAT GGTGATTTGA CTGCTCTCCGG CCTTTCTCAC CCGTTGAAAT CTTTACCTAC ACATTACTCA GGCATTGCAT TTAAAATATA 5600
5601 TGAGGGTTCT AAAAATTTTT ATCCTTGCGT TGAAATAAAG GCTTCTCCCG CAAAAGTATT ACAGGGTCAT AATGTTTTTG GTACAACCGA TTTAGCTTTA 5700
5701 TGCTCTGAGG CTTTATTGCT TAATTTTTGC CTTGCCTGTA TGATTTATTG TCGGCTGATG CGTATTTTTC TCCTTACGCA 5800
5801 TCTGTGCGGT ATTTCACACC GCATATGGTG CACTCTCAGT ACAATCTGCT CTGATGCCGC ATAGTTAAGC CAGCCCCGAC ACCCGCTGAC 5900
5901 GCGCCCTGAC GGGCTTGTCT GCTCCCGGCA TCCGCTTACA GACCGTCTCC GGGAGCTGCA TGTGTCAGAG GTTTTCACCG TCATCACCGA 6000
6001 AACGCGGCAG ACGAAAGGGC CTCGTGATAC GCCTATTTTT ATAGGTTAAT GTCATGATAA TAATGGTTTC TTAGACGTCA GGTGGCACTT TTCGGGGAAA 6100
6101 TCTGCGCGGA ACCCCTATTT GTTTATTTTT CTAAATACAT ATCCGCTCAT GAGACAATAA CCCTGATAAA TGCTTCAATA ATATTGAAAA 6200
6201 AGGAAGAGTA TGAGTATTCA ACATTTCCGT GTCGCCCTTA TTCCCTTTTT TGCGGCATTT TGCCTTCCTG TTTTTGCTCA CCCAGAAACG CTGGTGAAAG 6300
6301 TAAAAGATGC TGAAGATCAG TTGGGTGCAC GAGTGGGTTA CATCGAACTG GATCTCAACA GCGGTAAGAT CCTTGAGAGT TTTCGCCCCG AAGAACGTTT 6400
6401 TCCAATGATG AGCACTTTTA AAGTTCTGCT ATGTGGCGCG GTATTATCCC GTATTGACGC CGGGCAAGAG CAACTCGGTC GCCGCATACA CTATTCTCAG 6500
6501 AATGACTTGG TTGAGTACTC ACCAGTCACA GAAAAGCATC TTACGGATGG CATGACAGTA TTAAGCATTGGCC ACAACATGGG AGTGATAACA 6600
6601 CTGCGGCCAA CTTACTTCTG ACAACGATCG GAGGACCGAA GGAGCTAACC GCTTTTTTGC CTGTAGCAAT CTGTAGCCAAC GAAGCTACTT 6700
6701 ACCGGAGCTG AATGAAGCCA TACCAAACGA CGAGCGTGAC ACCACGATGC CTGTAGCAAT TGCCAACAAC CTTCTGCGCT CGGCCCTTCC GGCTGGCTGG TTTATTGCTG 6800
6801 ACTCTAGCTT CCCGGCAACA ATTAATAGAC TGGATGGAGG CGGATAAAGT TGCAGGACCA GGGCCAGAGTG GTAAGCCCTC CCGTATCGTA GTTATCTACA CGACGGGGAG 6900
6901 ATAAATCTGG AGCCGGTGAG CGTGGGTCTC GCGGTAACTG AAGTTCTGCT ATGCCGATATCAT AGTAGCACTGA CGTAGCCCTA GTAAGCCCTC CCGTATCGTA GTTATCTACA CGACGGGGAG 7000
7001 TCAGGCAACT ATGGATGAAC GAAATAGACA GATCGCTGAG ATGTCATCCA GATCGCTGAG CACTGATTAA GCATTGGTAA CGGGGGGTTC GTGCACACAG AAGTTTACTC ATATATACTT 7100
7101 TAGATTCATT TAAAACTTCA TTTTTAATTT AAAAGGATCT AGGTGAAGAT CCTTTTTTGAT AATCTCATGA CCAAAATCCC TTAACGTGAG TTTTCGTTCC 7200
7201 ACTGAGCGTC AGACCCCGTA GAAAAGATCA AAGGATCTTC TTGAGATCCT TTTTTTCTGC GCGTAATCTG CTGCTTGCAA ACAAAAAAAC CACCGCTACC 7300
7301 AGCGGTGGTT TGTTTGCCGG ATCAAGAGCT ACCAACTCTT TTTCCGAAGG TAACTGGCTT CAGCAGAGCG CAGATACCAA ATACTGTTCT TCTAGTGTAG 7400
7401 CCGTAGTTAG GCCACCACTT CAAGAACTCT GTAGCACCGC CTACATACCT CGCTCTGCTA ATCCTGTTAC CAGTGGCTGC TGCCAGTGGC GATAAGTCGT 7500
7501 GTCTTACCGG GTTGGACTCA AGACGATAGT TACCGGATAA GGCGCAGCGG TCGGGCTGAA CGGGGGGTTC GTGCACACAG CCCAGCTTGG AGCGAACGAC 7600
7601 CTACACCGAA CTGAGATACC TACAGCGTGA GCTATGAGAA AGCGCCACGC TTCCCGAAGG GAGAAAGGCG GACAGGTATC CGGTAAGCGG CAGGGTCGGA 7700
7701 ACAGGAGAGC GCACGAGGGA GCTTCCAGGG GGAAACGCCT GGTATCTTTA TAGTCCTGTC GGGTTTCGCC ACCTCTGACT TGAGCGTCGA TTTTTGTGAT 7800
7801 GCTCGTCAGG GGGGCGGAGC CTATGGAAAA ACGCCAGCAA CGCGGCCTTT TTACGGTTCC TGGCCTTTTG CTGGCCTTTT GCTCACATGT TCTTTCCTGC 7900
7901 GTTATCCCCT GATTCTGTGG ATAACCGTAT TACCGCCTTT GAGTGAGCTG ATACCGCTCG CCGCAGCCGA ACGACCGAGC GCAGCGAGTC AGTGAGCGAG 8000
8001 GAAGCGGAAG AGCGCCCAAT ACGCAAACCG CCTCTCCCCG CGCGTTGGCC GATTCATTAA TGCAGCTGGC CGCTCGCTGCG CTCACTGAGG CC 8092
                                                                                                       7700
    |        |        |        |        |        |        |        |        |        |
   10        20       30       40       50       60       70       80       90      100
```

What is claimed is:

1. An AAV vector for the expression of α-L-iduronidase, wherein the vector comprises (a) the nucleic acid coding sequence for α-L-iduronidase, as found in C.N.C.M. I-2892; (b) a phosphoglycerate kinase promoter; and (c) a woodchuck hepatitis virus posttranscriptional regulatory element, and wherein the coding sequence is operably linked to (b) and (c).

2. A method of transforming a brain cell of a mammal in vivo comprising: (a) providing a vector comprising: (i) a nucleic acid sequence encoding α-L-iduronidase, as found in C.N.C.M. I-2892; (ii) a phosphoglycerate kinase promoter; and (iii) a woodchuck hepatitis virus posttranscriptional regulatory element; and (b) delivering the vector to the brain of the mammal by stereotactic injection; wherein the nucleic acid, promoter, and regulatory element are in operable linkage, are encapsulated in an adenoassociated virus envelope, and the cell is local to the stereotactic injection site.

3. A cell transformed in vitro with the vector of claim 1, wherein the cell expresses α-L-iduronidase from the vector sequence.

4. A method of treating or preventing the accumulation of plaques associated with MPS I, wherein the method comprises administering by stereotactic injection, into the brain of the mammal, an AAV vector comprising (a) a phosphoglycerate kinase promoter sequence; (b) a woodchuck hepatitis virus posttranscriptional regulatory element; and (c) an α-L-iduronidase-encoding sequence operably linked to (a) and (b), wherein brain cells local to the injection site expresses α-L-iduronidase from the vector sequences.

5. A method of providing α-L-iduronidase to the brain of a mammal comprising administering, by stereotactic injection into the brain of the mammal, an AAV vector comprising (a) a sequence encoding α-L-iduronidase; (b) an operably linked phosphoglycerate kinse promoter sequences located upstream from (a); (c) an operably linked woodchuck hepatitis virus posttranscriptional regulatory element; and (d) two AAV terminal repeat sequences, flanking (a), (b), and (c); wherein the α-L-iduronidase is delivered to areas of the brain of the mammal distal to the injection site.

6. A purified nucleic acid molecule comprising (a) the α-L-iduronidase sequence contained in C.N.C.M. I-2892; (b) a phosphoglycerate kinse promoter located upstream from (a); (c) a woodchuck hepatitis virus posttranscriptional regulatory element; and (d) two AAV terminal repeat sequences flanking (a), (b), and (c), and wherein the nucleic acid molecule can express α-L-iduronidase.

* * * * *

SEQUENCE LISTING

<160> NUMBER OF SEQ ID NOS: 2

<210> SEQ ID NO 1
<211> LENGTH: 7648
<212> TYPE: DNA
<213> ORGANISM: Artificial Sequence
<220> FEATURE:
<223> OTHER INFORMATION: Description of Artificial Sequence: vector AAV-PGK-IDUA

<400> SEQUENCE: 1

| | | | | | |
|---|---|---|---|---|---|
| cagcagctgc | gcgctcgctc | gctcactgag | gccgcccggg | caaagcccgg | gcgtcgggcg | 60 |
| acctttggtc | gcccggcctc | agtgagcgag | cgagcgcgca | gagagggagt | ggccaactcc | 120 |
| atcactaggg | gttccttgta | gttaatgatt | aacccgccat | gctacttatc | tactcgagaa | 180 |
| ttctaccggg | tagggaggc | gcttttccca | aggcagtctg | gagcatgcgc | tttagcagcc | 240 |
| ccgctggcac | ttggcgctac | acaagtggcc | tctggcctcg | cacacattcc | acatccaccg | 300 |
| gtagcgccaa | ccggctccgt | tctttggtgg | ccccttcgcg | ccaccttcta | ctcctccct | 360 |
| agtcaggaag | ttccccccgc | cccgcagctc | gcgtcgtgca | ggacgtgaca | aatggaagta | 420 |
| gcacgtctca | ctagtctcgt | gcagatggac | agcaccgctg | agcaatggaa | gcgggtaggc | 480 |
| cttttgggca | gcggccaata | gcagctttgc | tccttcgctt | tctgggctca | gaggctggga | 540 |
| aggggtgggt | ccggggcgg | gctcagggc | gggctcaggg | gcgggcggg | cgcgaaggtc | 600 |
| ctccggagcc | cggcattctg | cacgcttcaa | aagcgcacgt | ctgccgcgct | gttctcctct | 660 |
| tcctcatctc | cgggccttc | gaccggatca | gatcgaattc | cccgaagccc | cgcagtcccc | 720 |
| gagcacgcgt | ggccatgcgt | cccctgcgcc | ccgcgccgc | gctgctggcg | ctcctggcct | 780 |
| cgctcctggc | cgcgcccccg | gtggcccgg | ccgaggcccc | gcacctggtg | catgtggacg | 840 |
| cggcccgcgc | gctgtgggcc | ctgcggcgct | tctggaggag | cacaggcttc | tgccccccgc | 900 |
| tgccacacag | ccaggctgac | cagtacgtcc | tcagctggga | ccagcagctc | aacctcgcct | 960 |
| atgtgggcgc | cgtccctcac | cgcggcatca | agcaggtccg | gacccactgg | ctgctggagc | 1020 |
| ttgtcaccac | caggggtcc | actggacggg | gcctgagcta | caacttcacc | cacctggacg | 1080 |
| ggtacttgga | ccttctcagg | gagaaccagc | tcctcccagg | gtttgagctg | atgggcagcg | 1140 |
| cctcgggcca | cttcactgac | tttgaggaca | agcaggtgtt | tgagtggaag | gacttggtct | 1200 |
| ccagcctggc | caggagatac | atcggtaggt | acggactggc | gcatgtttcc | aagtggaact | 1260 |
| tcgagacgtg | gaatgagcca | gaccaccacg | actttgacaa | cgtctccatg | accatgcaag | 1320 |
| gcttcctgaa | ctactacgat | gcctgctcgg | agggtctgcg | cgccgccagc | cccgccctgc | 1380 |
| ggctgggagg | ccccggcgac | tccttccaca | ccccaccgcg | atccccgctg | agctggggcc | 1440 |
| tcctgcgcca | ctgccacgac | ggtaccaact | tcttcactgg | ggaggcgggc | gtgcggctgg | 1500 |
| actacatctc | cctccacagg | aagggtgcgc | gcagctccat | ctccatcctg | gagcaggaga | 1560 |
| aggtcgtcgc | gcagcagatc | cggcagctct | tccccaagtt | cgcggacacc | cccatttaca | 1620 |
| acgacgaggc | ggaccgctg | gtgggctggt | ccctgccaca | gccgtggagg | gcggacgtga | 1680 |
| cctacgcggc | catggtggtg | aaggtcatcg | cgcagcatca | gaacctgcta | ctggccaaca | 1740 |
| ccacctccgc | cttccccctac | gcgctcctga | gcaacgacaa | tgccttcctg | agctaccacc | 1800 |
| cgcaccctt | cgcgcagcgc | acgctcaccg | cgcgcttcca | ggtcaacaac | acccgcccgc | 1860 |
| cgcacgtgca | gctgttgcgc | aagccggtgc | tcacggccct | ggggctgctg | gcgctgctgg | 1920 |

-continued

```
atgaggagca gctctgggcc gaagtgtcgc aggccgggac cgtcctggac agcaaccaca    1980
cggtgggcgt cctggccagc gcccaccgcc cccaggggcc ggccgacgcc tggcgcgccg    2040
cggtgctgat ctacgcgagc gacgacaccc gcgcccaccc caaccgcagc gtcgcggtga    2100
ccctgcggct gcgcggggtg ccccccggcc cgggcctggt ctacgtcacg cgctacctgg    2160
acaacgggct ctgcagcccc gacggcgagt ggcggcgcct gggccggccc gtcttcccca    2220
cggcagagca gttccggcgc atgcgcgcgg ctgaggaccc ggtggccgcg gcgcccgcc     2280
ccttacccgc cggcggccgc ctgaccctgc gccccgcgct gcggctgccg tcgcttttgc    2340
tggtgcacgt gtgtgcgcgc cccgagaagc gcccgggca ggtcacgcgg ctccgcgccc     2400
tgcccctgac ccaagggcag ctggttctgg tctggtcgga tgaacacgtg ggctccaagt    2460
gcctgtggac atacgagatc cagttctctc aggacggtaa ggcgtacacc ccggtcagca    2520
ggaagccatc gaccttcaac ctctttgtgt tcagcccaga cacaggtgct gtctctggct    2580
cctaccgagt tcgagccctg gactactggg cccgaccagg ccccttctcg accctgtgc     2640
cgtacctgga ggtccctgtg ccaagagggc ccccatcccc gggcaatcca tgagcctgtg    2700
ctgagcccca gtgggttggc gattagtcca atttgttaaa gacaggatat cagtggtcca    2760
ggctctagtt ttgactcaac aatatcacca gctgaagcct atagagtacg agccatagat    2820
aaaataaaag attttattta gtctccagaa aaaggggga atgaaagacc ccacctgtag     2880
gtttggcaag ctagtctagt aacggccgcc agtgtgctgg aattctgcag atatccatca    2940
cactggcggc cgctcgagca tgcatctaga gcgataatca acctctggat tacaaaattt    3000
gtgaaagatt gactggtatt cttaactatg ttgctccttt tacgctatgt ggatacgctg    3060
ctttaatgcc tttgtatcat gctattgctt cccgtatggc tttcattttc tcctccttgt    3120
ataaatcctg gttgctgtct ctttatgagg agttgtggcc cgttgtcagg caacgtggcg    3180
tggtgtgcac tgtgtttgct gacgcaaccc ccactggttg gggcattgcc accacctgtc    3240
agctcctttc cgggactttc gctttccccc tccctattgc cacggcggaa ctcatcgccg    3300
cctgccttgc ccgctgctgg acaggggctc ggctgttggg cactgacaat tccgtggtgt    3360
tgtcggggaa gctgacgtcc tttccatggc tgctcgcctg tgttgccacc tggattctgc    3420
gcgggacgtc cttctgctac gtcccttcgg ccctcaatcc agcggacctt ccttcccgcg    3480
gcctgctgcc ggctctgcgg cctcttccgc gtcttcgcct tcgccctgag acgagtcgga    3540
tctccctttg ggccgcctcc ccgcatcgct attctatagt gtcacctaaa tgctagagct    3600
cgctgatcag cctcgactgt gccttctagt tgccagccat ctgttgtttg ccctccccc     3660
gtgccttcct tgaccctgga agtgccact cccactgtcc tttcctaata aaatgaggaa     3720
attgcatcgc attgtctgag taggtgtcat tctattctgg ggggtggggt ggggcaggac    3780
agcaagggggg aggattggga agacaatagc aggcatgctg gggatgcggt gggctctatg   3840
gcttctgagg cggaaagaac caggtagata agtagcatgg cgggttaatc attaactaca    3900
aggaacccct agtgatggag ttggccactc cctctctgcg cgctcgctcg ctcactgagg    3960
ccgggcgacc aaaggtcgcc cgacgcccgg gctttgcccg gcggcctcaa gtgagcgagc    4020
gagcgcgcag ctggcgtaat agcgaagagg cccgcaccga tcgcccttcc caacagttgc    4080
gcagcctgaa tggcgaatgg cgattccgtt gcaatggctg gcgtaatat tgttctggat     4140
attaccagca aggccgatag tttgagttct tctactcagg caagtgatgt tattactaat    4200
caaagaagta ttgcgacaac ggttaatttg cgtgatggac agactctttt actcggtggc    4260
ctcactgatt ataaaaacac ttctcaggat tctggcgtac cgttcctgtc taaaatccct    4320
```

```
ttaatcggcc tcctgtttag ctcccgctct gattctaacg aggaaagcac gttatacgtg    4380
ctcgtcaaag caaccatagt acgcgccctg tagcggcgca ttaagcgcgg cgggtgtggt    4440
ggttacgcgc agcgtgaccg ctacacttgc cagcgcccta cgcccgctc ctttcgcttt     4500 cttcccttcc tttctcgcca cgttcgccgg ctttccccgt caagctctaa atcgggggct    4560 cccttaggg ttccgattta gtgctttacg gcacctcgac cccaaaaaac ttgattaggg     4620
tgatggttca cgtagtgggc catcgccctg atagacggtt tttcgccctt tgacgttgga    4680
gtccacgttc tttaatagtg gactcttgtt ccaaactgga acaacactca accctatctc    4740
ggtctattct tttgatttat aagggatttt gccgatttcg gcctattggt taaaaaatga    4800
gctgatttaa caaaaattta acgcgaattt taacaaaata ttaacgctta caatttaaat    4860
atttgcttat acaatcttcc tgttttttggg gcttttctga ttatcaaccg ggtacatat    4920 gattgacatg ctagttttac gattaccgtt catcgattct cttgtttgct ccagactctc    4980
aggcaatgac ctgatagcct tgtagagac ctctcaaaaa tagctaccct ctccggcatg     5040
aatttatcag ctagaacggt tgaatatcat attgatggtg atttgactgt ctccggcctt    5100
tctcacccgt ttgaatcttt acctacacat tactcaggca ttgcatttaa aatatatgag    5160
ggttctaaaa atttttatcc ttgcgttgaa ataaaggctt ctcccgcaaa agtattacag    5220
ggtcataatg ttttttggtac aaccgattta gctttatgct ctgaggcttt attgcttaat    5280
tttgctaatt ctttgccttg cctgtatgat ttattggatg ttggaatcgc ctgatgcggt    5340
attttctcct tacgcatctg tgcggtattt cacaccgcat atggtgcact ctcagtacaa    5400
tctgctctga tgccgcatag ttaagccagc cccgacaccc gccaacaccc gctgacgcgc    5460
cctgacgggc ttgtctgctc ccggcatccg cttacagaca agctgtgacc gtctccggga    5520
gctgcatgtg tcagaggttt tcaccgtcat caccgaaacg cgcgagacga aagggcctcg    5580
tgatacgcct attttatag gttaatgtca tgataataat ggtttcttag acgtcaggtg     5640
gcacttttcg gggaaatgtg cgcggaaccc ctatttgttt attttttctaa atacattcaa    5700 atatgtatcc gctcatgaga caataaccct gataaatgct tcaataatat tgaaaaagga    5760
agagtatgag tattcaacat ttccgtgtcg cccttattcc cttttttgcg gcattttgcc    5820
ttcctgtttt tgctcaccca gaaacgctgg tgaaagtaaa agatgctgaa gatcagttgg    5880
gtgcacgagt gggttacatc gaactggatc tcaacagcgg taagatcctt gagagttttc    5940
gccccgaaga acgttttcca atgatgagca cttttaaagt tctgctatgt ggcgcggtat    6000
tatcccgtat tgacgccggg caagagcaac tcggtcgccg catacactat tctcagaatg    6060
acttggttga gtactcacca gtcacagaaa agcatcttac ggatggcatg acagtaagag    6120
aattatgcag tgctgccata accatgagtg ataacactgc ggccaactta cttctgacaa    6180
cgatcggagg accgaaggag ctaaccgctt ttttgcacaa catgggggat catgtaactc    6240
gccttgatcg ttgggaaccg gagctgaatg aagccatacc aaacgacgag cgtgacacca    6300
cgatgcctgt agcaatggca acaacgttgc gcaaactatt aactggcgaa ctacttactc    6360
tagcttcccg gcaacaatta atagactgga tggaggcgga taaagttgca ggaccacttc    6420
tgcgctcggc ccttccggct ggctggttta ttgctgataa atctggagcc ggtgagcgtg    6480
ggtctcgcgg tatcattgca gcactggggc cagatggtaa gccctcccgt atcgtagtta    6540
tctacacgac ggggagtcag gcaactatgg atgaacgaaa tagacagatc gctgagatag    6600
gtgcctcact gattaagcat tggtaactgt cagaccaagt ttactcatat atactttaga    6660
```

```
ttgatttaaa acttcatttt taatttaaaa ggatctaggt gaagatcctt tttgataatc    6720
tcatgaccaa atcccttaa cgtgagtttt cgttccactg agcgtcagac cccgtagaaa    6780
agatcaaagg atcttcttga gatccttttt ttctgcgcgt aatctgctgc ttgcaaacaa    6840
aaaaaccacc gctaccagcg gtggtttgtt tgccggatca agagctacca actctttttc    6900
cgaaggtaac tggcttcagc agagcgcaga taccaaatac tgttcttcta gtgtagccgt    6960
agttaggcca ccacttcaag aactctgtag caccgcctac atacctcgct ctgctaatcc    7020
tgttaccagt ggctgctgcc agtggcgata agtcgtgtct taccgggttg gactcaagac    7080
gatagttacc ggataaggcg cagcggtcgg gctgaacggg gggttcgtgc acacagccca    7140
gcttggagcg aacgacctac accgaactga gatacctaca gcgtgagcta tgagaaagcg    7200
ccacgcttcc cgaagggaga aaggcggaca ggtatccggt aagcggcagg gtcggaacag    7260
gagagcgcac gagggagctt ccagggggga acgcctggta tctttatagt cctgtcgggt    7320
ttcgccacct ctgacttgag cgtcgatttt tgtgatgctc gtcaggggg cggagcctat    7380 ggaaaaacgc cagcaacgcg gcctttttac ggttcctggc cttttgctgg ccttttgctc    7440
acatgttctt tcctgcgtta tcccctgatt ctgtggataa ccgtattacc gcctttgagt    7500
gagctgatac cgctcgccgc agccgaacga ccgagcgcag cgagtcagtg agcgaggaag    7560
cggaagagcg cccaatacgc aaaccgcctc tccccgcgcg ttggccgatt cattaatgca    7620
gctgcgcgct cgctcgctca ctgaggcc                                      7648
```

<210> SEQ ID NO 2
<211> LENGTH: 8092
<212> TYPE: DNA
<213> ORGANISM: Artificial Sequence
<220> FEATURE:
<223> OTHER INFORMATION: Description of Artificial Sequence: vector
    AAV-PGK-NaGLU

<400> SEQUENCE: 2

```
cagcagctgc gcgctcgctc gctcactgag gccgcccggg caaagcccgg gcgtcgggcg      60
acctttggtc gcccggcctc agtgagcgag cgagcgcgca gagagggagt ggccaactcc     120
atcactaggg gttccttgta gttaatgatt aacccgccat gctacttatc tactcgagaa     180
ttctaccggg taggggaggc gcttttccca aggcagtctg gagcatgcgc tttagcagcc     240
ccgctggcac ttggcgctac acaagtggcc tctggcctcg cacacattcc acatccaccg     300
gtagcgccaa ccggctccgt tctttggtgg ccccttcgcg ccaccttcta ctcctcccct     360
agtcaggaag ttccccccgc cccgcagctc gcgtcgtgca ggacgtgaca aatggaagta     420
gcacgtctca ctagtctcgt gcagatggac agcaccgctg agcaatggaa gcgggtaggc     480
ctttggggca gcggccaata gcagctttgc tccttcgctt tctgggctca gaggctggga     540
aggggtgggt ccggggcgg gctcagggc gggctcaggg gcgggcggg gcgcgaaggtc      600 ctccggagcc cggcattctg cacgcttcaa agcgcacgt ctgccgcgct gttctcctct     660
tcctcatctc cgggccttc gaccggatcc cccgggctgc aggaattccg agaccatgga     720
ggcggtggcg gtggccgcgg cggtgggggt ccttctcctg gccggggccg ggggcgcggc     780
aggcgacgag gcccggagg cggcggccgt gcgggcgctc gtggcccggc tgctggggcc     840
aggccccgcg gccgacttct ccgtgtcggt ggagcgcgct ctggctgcca agccgggctt     900
ggacacctac agcctgggcg gcggcggcgc ggcgcgcgtg cgggtgcgcg gctcccacggg    960 cgtggcggcc gccgcggggc tgcaccgcta cctgcgcgac ttctgtggct gccacgtggc    1020
```

```
ctggtccggc tctcagctgc gcctgccgcg gccactgcca gccgtgccgg gggagctgac    1080
cgaggccacg cccaacaggt accgctatta ccagaatgtg tgcacgcaaa gctactcctt    1140
cgtgtggtgg gactgggccc gctgggagcg agagatagac tggatggcgc tgaatggcat    1200
caacctggca ctggcctgga gcggccagga ggccatctgg cagcgggtgt acctggcctt    1260
gggcctgacc caggcagaga tcaatgagtt ctttactggt cctgccttcc tggcctgggg    1320
gcgaatgggc aacctgcaca cctgggatgg cccctgccc cctcctggc acatcaagca    1380 gctttacctg cagcaccggg tcctggacca gatgcgctcc ttcggcatga ccccagtgct    1440
gcctgcattc gcggggcatg ttcccgaggc tgtcaccagg tgttccctc aggtcaatgt    1500 cacgaagatg ggcagttggg gccactttaa ctgttcctac tcctgctcct tccttctggc    1560 tccgaagac cccatattcc ccatcatcgg gagcctcttc ctgcgagagc tgatcaaaga    1620
gtttggcaca gaccacatct atggggccga cactttcaat gagatgcagc accttcctc    1680 agagccctcc taccttgccg cagccaccac tgccgtctat gaggccatga ctgcagtgga    1740
tactgaggct gtgtggctgc tccaaggctg gctcttccag caccagccgc agttctgggg    1800
gcccgcccag atcagggctg tgctgggagc tgtgccccgt ggccgcctcc tggttctgga    1860
cctgtttgct gagagccagc ctgtgtatac ccgcactgcc tccttccagg gccagccctt    1920
catctggtgc atgctgcaca actttggggg aaaccatggt ctttttggag ccctagaggc    1980
tgtgaacgga ggcccagaag ctgcccgcct cttccccaac tccaccatgg taggcacggg    2040
catggccccc gagggcatca gccagaacga agtggtctat tccctcatgg ctgagctggg    2100
ctggcgaaag gaccagctgc cagatttggc agcctgggtg accagctttg ccgcccggcg    2160
gtatggggtc tccccacccg gacgcagggg agcgtggagg ctactgctcc ggagtgtgta    2220
caactgctcc ggggaggcct gcaggggcca caatcgtagc ccgctggtca ggcggccgtc    2280
cctacagatg aataccagca tctggtacaa ccgatctgat gtgtttgagg cctggcggct    2340
gctgctcaca tctgctccct ccctggccac cagccccgcc ttccgctacg acctgctgga    2400
cctcactcgg caggcagtgc aggagctggt cagcttgtac tatgaggagg caagaagcgc    2460
ctacctgagc aaggagctgg cctccctgtt gagggctgga ggcgtcctgg cctatgagct    2520
gctgccggca ctggacgagg tgctggctag tgacagccgc ttcttgctgg cagctggct    2580 agagcaggcc cgagcagcgg cagtcagtga ggccgaggcc gatttctacg agcagaacag    2640
ccgctaccag ctgaccttgt gggggccaga aggcaacatc ctggactatg ccaacaagca    2700
gctggcgggg ttggtggcca actactacac ccctcgctgg cggcttttcc tggaggcgct    2760
ggttgacagt gtgcccagg gcatcccttt ccaacagcac cagtttgaca aaaatgtctt    2820
ccaactggag caggccttcg ttctcagcaa gcagaggtac cccagccagc cgcgaggaga    2880
cactgtggac ctggccaaga agatcttcct caaatattac cccggctggg tggccggctc    2940
ttggtgatag attcgccacc actgggcctt gttttccgct aattccaggg cagattccag    3000
ggcccagagc tggacagaca tcacaggata cccaggcct gggaggaggc cccacggcct    3060
gctggtgggg tctgacctgg ggggattgga gggaaatgac ctgccctcca ccaccaccca    3120
aagtgtggga ttaaagtagc ttggtaccga gctcggatcc ggcgattagt ccaatttgtt    3180
aaagacagga tatcagtggt ccaggctcta gttttgactc aacaatatca ccagctgaag    3240
cctatagagt acgagccata gataaaataa agatttttat ttagtctcca gaaaagggg    3300 ggaatgaaag accccacctg taggtttggc aagctagcgc tagtaacggc cgccagtgtg    3360
ctggaattct gcagatatcc atcacactgg cggccgctcg agcatgcatc tagagcgata    3420
```

-continued

```
atcaacctct ggattacaaa atttgtgaaa gattgactgg tattcttaac tatgttgctc    3480
cttttacgct atgtggatac gctgctttaa tgcctttgta tcatgctatt gcttcccgta    3540
tggctttcat tttctcctcc ttgtataaat cctggttgct gtctctttat gaggagttgt    3600
ggcccgttgt caggcaacgt ggcgtggtgt gcactgtgtt tgctgacgca accccactg    3660 gttgggcat tgccaccacc tgtcagctcc tttccgggac tttcgctttc ccctccta      3720 ttgccacggc ggaactcatc gccgcctgcc ttgcccgctg ctggacaggg gctcggctgt    3780
tgggcactga caattccgtg gtgttgtcgg ggaagctgac gtccttcca tggctgctcg     3840 cctgtgttgc cacctggatt ctgcgcggga cgtccttctg ctacgtccct tcggccctca    3900
atccagcgga ccttccttcc cgcggcctgc tgccggctct gcggcctctt ccgcgtcttc    3960
gccttcgccc tgagacgagt cggatctccc tttgggccgc ctccccgcat cgctattcta    4020
tagtgtcacc taaatgctag agctcgctga tcagcctcga ctgtgccttc tagttgccag    4080
ccatctgttg tttgcccctc cccgtgcct tccttgaccc tggaaggtgc cactcccact     4140
gtcctttcct aataaaatga ggaaattgca tcgcattgtc tgagtaggtg tcattctatt    4200
ctggggggtg gggtggggca ggacagcaag ggggaggatt gggaagacaa tagcaggcat    4260 gctgggatg cggtgggctc tatggcttct gaggcggaaa gaaccaggta gataagtagc     4320
atggcgggtt aatcattaac tacaaggaac ccctagtgat ggagttggcc actccctctc    4380
tgcgcgctcg ctcgctcact gaggccgggc gaccaaaggt cgcccgacgc ccgggctttg    4440
cccgggcggc ctcagtgagc gagcgagcgc gcagctggcg taatagcgaa gaggcccgca    4500
ccgatcgccc ttcccaacag ttgcgcagcc tgaatggcga atggcgattc cgttgcaatg    4560
gctggcggta atattgttct ggatattacc agcaaggccg atagtttgag ttcttctact    4620
caggcaagtg atgttattac taatcaaaga agtattgcga caacggttaa tttgcgtgat    4680
ggacagactc ttttactcgg tggcctcact gattataaaa acacttctca ggattctggc    4740
gtaccgttcc tgtctaaaat ccctttaatc ggcctcctgt ttagctcccg ctctgattct    4800
aacgaggaaa gcacgttata cgtgctcgtc aaagcaacca tagtacgcgc cctgtagcgg    4860
cgcattaagc gcggcgggtg tggtggttac gcgcagcgtg accgctacac ttgccagcgc    4920
cctagcgccc gctcctttcg ctttcttccc ttcctttctc gccacgttcg ccggcttttcc   4980 ccgtcaagct ctaaatcggg ggctcccttt agggttccga tttagtgctt tacggcacct    5040
cgaccccaaa aaacttgatt aggtgatgg ttcacgtagt gggccatcgc cctgatagac     5100 ggttttttcgc cctttgacgt tggagtccac gttctttaat agtggactct gttccaaac    5160 tggaacaaca ctcaaccta tctcggtcta ttcttttgat ttataaggga ttttgccgat     5220
ttcggcctat tggttaaaaa atgagctgat ttaacaaaaa tttaacgcga attttaacaa    5280
aatattaacg cttacaattt aaatatttgc ttatacaatc ttcctgtttt tggggctttt    5340
ctgattatca accgggtac atatgattga catgctagtt ttacgattac cgttcatcga     5400
ttctcttgtt tgctccagac tctcaggcaa tgacctgata gcctttgtag agacctctca    5460
aaaatagcta ccctctccgg catgaattta tcagctagaa cggttgaata tcatattgat    5520
ggtgatttga ctgtctccgg cctttctcac ccgtttgaat cttacctac acattactca     5580 ggcattgcat ttaaaatata tgagggttct aaaaattttt atccttgcgt tgaaataaag    5640
gcttctcccg caaagtatt acagggtcat aatgttttg gtacaaccga tttagcttta     5700
tgctctgagg ctttattgct taattttgct aattctttgc cttgcctgta tgatttattg   5760
```

```
gatgttggaa tcgcctgatg cggtattttc tccttacgca tctgtgcggt atttcacacc    5820
gcatatggtg cactctcagt acaatctgct ctgatgccgc atagttaagc cagccccgac    5880
acccgccaac acccgctgac gcgccctgac gggcttgtct gctcccggca tccgcttaca    5940
gacaagctgt gaccgtctcc gggagctgca tgtgtcagag gttttcaccg tcatcaccga    6000
aacgcgcgag acgaaagggc ctcgtgatac gcctattttt ataggttaat gtcatgataa    6060
taatggtttc ttagacgtca ggtggcactt ttcggggaaa tgtgcgcgga acccctattt    6120
gtttattttt ctaaatacat tcaaatatgt atccgctcat gagacaataa ccctgataaa    6180
tgcttcaata atattgaaaa aggaagagta tgagtattca catttccgt gtcgcccta    6240 ttccctttt tgcggcattt tgccttcctg ttttttgctca cccagaaacg ctggtgaaag    6300
taaaagatgc tgaagatcag ttgggtgcac gagtgggtta catcgaactg gatctcaaca    6360
gcggtaagat ccttgagagt tttcgccccg aagaacgttt tccaatgatg agcactttta    6420
aagttctgct atgtggcgcg gtattatccc gtattgacgc cgggcaagag caactcggtc    6480
gccgcataca ctattctcag aatgacttgg ttgagtactc accagtcaca gaaaagcatc    6540
ttacggatgg catgacagta agagaattat gcagtgctgc cataaccatg agtgataaca    6600
ctgcggccaa cttacttctg acaacgatcg gaggaccgaa ggagctaacc gcttttttgc    6660
acaacatggg ggatcatgta actcgccttg atcgttggga accggagctg aatgaagcca    6720
taccaaacga cgagcgtgac accacgatgc ctgtagcaat ggcaacaacg ttgcgcaaac    6780
tattaactgg cgaactactt actctagctt cccggcaaca attaatagac tggatggagg    6840
cggataaagt tgcaggacca cttctgcgct cggcccttcc ggctggctgg tttattgctg    6900
ataaatctgg agccggtgag cgtgggtctc gcggtatcat tgcagcactg gggccagatg    6960
gtaagccctc ccgtatcgta gttatctaca cgacggggag tcaggcaact atggatgaac    7020
gaaatagaca gatcgctgag ataggtgcct cactgattaa gcattggtaa ctgtcagacc    7080
aagtttactc atatatactt tagattgatt taaaacttca tttttaattt aaaaggatct    7140
aggtgaagat cctttttgat aatctcatga ccaaaatccc ttaacgtgag ttttcgttcc    7200
actgagcgtc agaccccgta gaaaagatca aaggatcttc ttgagatcct ttttttctgc    7260
gcgtaatctg ctgcttgcaa acaaaaaaac caccgctacc agcggtggtt tgtttgccgg    7320
atcaagagct accaactctt tttccgaagg taactggctt cagcagagcg cagataccaa    7380
atactgttct tctagtgtag ccgtagttag gccaccactt caagaactct gtagcaccgc    7440
ctacatacct cgctctgcta atcctgttac cagtggctgc tgccagtggc gataagtcgt    7500
gtcttaccgg gttggactca agacgatagt taccggataa ggcgcagcgg tcgggctgaa    7560
cggggggttc gtgcacacag cccagcttgg agcgaacgac ctacaccgaa ctgagatacc    7620
tacagcgtga gctatgagaa agcgccacgc ttcccgaagg gagaaaggcg gacaggtatc    7680
cggtaagcgg cagggtcgga acaggagagc gcacagggga gcttccaggg ggaaacgcct    7740
ggtatcttta tagtcctgtc gggtttcgcc acctctgact tgagcgtcga ttttgtgat    7800 gctcgtcagg gggcggagc ctatggaaaa acgccagcaa cgcggccttt ttacggttcc    7860
tggccttttg ctggccttt gctcacatgt tctttcctgc gttatcccct gattctgtgg    7920
ataaccgtat taccgccttt gagtgagctg ataccgctcg ccgcagccga acgaccgagc    7980
gcagcgagtc agtgagcgag gaagcggaag agcgcccaat acgcaaaccg cctctccccg    8040
cgcgttggcc gattcattaa tgcagctgcg cgctcgctcg ctcactgagg cc            8092
```